United States Patent [19]

Shibata et al.

[11] Patent Number: 5,035,739

[45] Date of Patent: Jul. 30, 1991

[54] TRIFLUOROMETHANESULFONAMIDE DERIVATIVE AND A HERBICIDE CONTAINING THE SAME

[75] Inventors: Mitsuru Shibata; Yoshiyuki Hiramatsu; Ryoichi Adachi; Kenichiro Mitsutake, all of Chiba, Japan

[73] Assignee: Idemitsu Kosan Company Limited, Tokyo, Japan

[21] Appl. No.: 471,108

[22] Filed: Jan. 26, 1990

Related U.S. Application Data

[62] Division of Ser. No. 254,935, Sep. 6, 1988, Pat. No. 4,919,705.

[30] Foreign Application Priority Data

Feb. 10, 1987 [JP] Japan .................................. 62-27127
Jul. 27, 1987 [JP] Japan .................................. 62-185380

[51] Int. Cl.$^5$ .................... A01N 43/16; A01N 43/18; C07D 309/14; C07D 335/06
[52] U.S. Cl. ................................ 71/91; 71/88; 71/90; 549/23; 549/404
[58] Field of Search ................. 549/23, 404; 71/88, 71/90, 91

[56] References Cited

U.S. PATENT DOCUMENTS

3,629,332 12/1971 Harrington et al. .................. 564/97
4,244,960 1/1981 Schroder et al. .................... 546/293

FOREIGN PATENT DOCUMENTS

0207614 1/1987 European Pat. Off. .
47-27954 10/1972 Japan .
61-221170 10/1986 Japan .

Primary Examiner—Mary C. Lee
Assistant Examiner—Jacqueline Haley
Attorney, Agent, or Firm—Frishauf, Holtz, Goodman & Woodward

[57] ABSTRACT

The present invention relates to a trifluoromethanesulfonamide derivative represented by the general formula given below, a herbicide with the derivative as the active ingredient and a method for the preparation of the derivative.

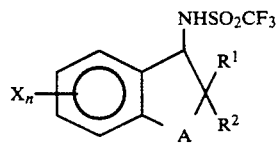

[In the formula, X is a hydrogen atom, a halogen atom, an alkyl group having 1 to 4 carbon atoms or a haloalkyl group having 1 to 4 carbon atoms, n is 1, 2 or 3 and A is $-O-CR^3R^4-$, $-S-CR^3R^4-$, $-SO-CR^3R^4-$, $-SO_2-CR^3R^4-$ or $-SO_2-NR^3-$. And, $R^1$, $R^2$, $R^3$ and $R^4$ are each a hydrogen atom or an alkyl group having 1 to 4 carbon atoms.]

These compounds are prepared depending on A in the above given general formula by the reaction of an amine derivative and a trifluoromethanesulfonyl halide or trifluoromethanesulfonic anhydride or by the oxidation of a thiochroman ring-containing trifluoromethanesulfonamide derivative.

Further, these trifluoromethanesulfonamide derivatives are useful as a herbicide and serve to weeding of weeds without phytotoxicity against crops in upland field. These trifluoromethanesulfonamide derivatives can also be used as a plant growth regulator.

30 Claims, No Drawings

TRIFLUOROMETHANESULFONAMIDE DERIVATIVE AND A HERBICIDE CONTAINING THE SAME

This is a division of application Ser. No. 07/254,935 filed Sept. 6, 1988, now U.S. Pat. No. 4,919,705, issued Apr. 24, 1990, which is the United States designated application of PCT/JP88/00104 filed Feb. 4, 1988.

FIELD OF TECHNOLOGY

The present invention relates to a novel trifluoromethanesulfonamide derivative, a method for the preparation thereof and a herbicide containing the same.

BACKGROUND TECHNOLOGY

It is known that benzylamine-type trifluoromethanesulfonamide derivatives such as N-benzyltrifluoromethanesulfonamide and the like and trifluoromethanesulfonamide derivatives having a condensed heterocyclic ring structure have herbicidal activity so that they are used as a herbicide.

These compounds, however, have no sufficiently high herbicidal activity against troublesome weeds and common weeds in upland field and, in an addition, have a problem in respect of the phytotoxicity to crops.

A first object of the present invention is to provide a herbicide containing a novel trifluoromethanesulfonamide derivative as the active ingredient having, by solving the problem of the phytotoxicity to crops, sufficiently high herbicidal activity against weeds including purple nutsedge, i.e. *Cyperus rotundus*, and safety for crops in an upland field such as soybean, cotton, maize and the like.

A second object of the present invention is to provide the novel trifluoromethanesulfonamide derivative used as the active ingredient of the above mentioned herbicide and an efficient method for the preparation thereof.

DISCLOSURE OF THE INVENTION

The present invention provides: (1) a trifluoromethanesulfonamide derivative represented by the general formula

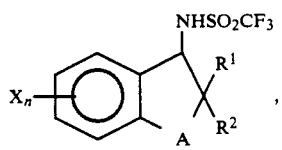

in which X is a hydrogen atom, a halogen atom, an alkyl group having 1 to 4 carbon atoms or a haloalkyl group having 1 to 4 carbon atoms, n is 1, 2 or 3, A is $-O-CR^3R^4-$, $-S-CR^3R^4-$, $-SO-CR^3R^4-$, $-SO_2-CR^3R^4-$ or $-SO_2-NR^3-$, and $R^1$, $R^2$, $R^3$ and $R^4$ are each a hydrogen atom or an alkyl group having 1 to 4 carbon atoms;

(2) a method for the preparation of a trifluoromethanesesulfonamide derivative represented by the general formula

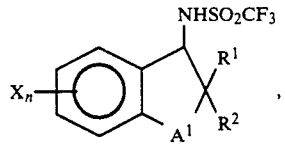

in which X, n, $R^1$, $R^2$ and $A^1$ each have the same meaning as defined below, characterized by reacting an amine derivative represented by the general formula

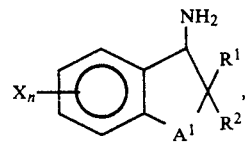

in which X is a hydrogen atom, a halogen atom, an alkyl group having 1 to 4 carbon atoms or a haloalkyl group having 1 to 4 carbon atoms, n is 1, 2 or 3, $A^1$ is $-O-CR^3R^4-$, $-S-CR^3R^4-$ or $-SO_2-NR^3-$ and $R^1$, $R^2$, $R^3$ and $R^4$ are each a hydrogen atom or an alkyl group having 1 to 4 carbon atoms, and a trifluoromethanesulfonyl halide or trifluoromethanesulfonic anhydride;

(3) a method for the preparation of a trifluoromethanesulfonamide derivative represented by the general formula

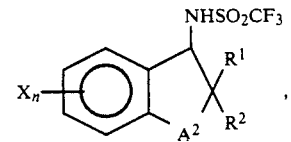

in which X is a hydrogen atom, a halogen atom, an alkyl group having 1 to 4 carbon atoms or a haloalkyl group having 1 to 4 carbon atoms, n is 1, 2 or 3, $A^2$ is $-SO-CR^3R^4-$ or $-SO_2-CR^3R^4-$, and $R^1$, $R^2$, $R^3$ and $R^4$ are each a hydrogen atom or an alkyl group having 1 to 4 carbon atoms, characterized by oxidizing a trifluoromethanesulfonamide derivative having a thiochroman ring represented by the general formula

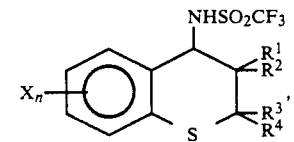

in which X is a hydrogen atom, a halogen atom, an alkyl group having 1 to 4 carbon atoms or a haloalkyl group having 1 to 4 carbon atoms, n is 1, 2 or 3 and $R^1$, $R^2$, $R^3$ and $R^4$ are each a hydrogen atom or an alkyl group having 1 to 4 carbon atoms; and (4) a herbicide containing a trifluoromethanesulfonamide derivative represented by the general formula

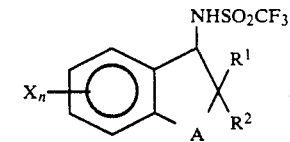

in which X is a hydrogen atom, a halogen atom, an alkyl group having 1 to 4 carbon atoms or a haloalkyl group having 1 to 4 carbon atoms, n is 1, 2 or 3, A is —O—CR³R⁴—, —S—CR³R⁴—, —SO—CR³R⁴—, —SO₂—CR³R⁴— or SO₂NR³—, and R¹, R², R³ and R⁴ are each a hydrogen atom or an alkyl group having 1 to 4 carbon atoms.

The trifluoromethanesulfonamide derivatives of the present invention are each a novel compound and can be used effectively as a herbicide. Further, the trifluoromethanesulfonamide derivatives can be prepared efficiently in a high purity and in a high yield according to the method of the present invention.

The herbicide of the present invention can exhibit the effectiveness in either of the treating methods including the soil treatment and foliar treatment. Further, this herbicide has an excellent herbicidal effect against purple nutsedge known as a hardly controllable weed as compared with hitherto marketed herbicides such as Perfluidone, Alachlor and the like and can exhibit a sufficiently high herbicidal effect against other weeds even in a low dose. Furthermore, the herbicide of the present invention has no phytotoxicity even in a high dose against crops such as soybean, cotton, maize and the like so that it is applicable to these crops with safety and widely usable as a herbicide in non-plowed fields and as a plant growth regulator.

BEST MODE FOR EMBODIMENTS TO PRACTICE THE INVENTION

The present invention provides a trifluoromethanesulfonamide derivative represented by the general formula

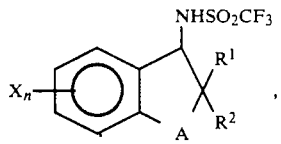

[I]

in which X is a hydrogen atom, a halogen atom, an alkyl group having 1 to 4 carbon atoms or a haloalkyl group having 1 to 4 carbon atoms, n is 1, 2 or 3, A is —O—CR³R⁴—, —S—CR³R⁴—, —SO—CR³R⁴—, —SO₂—CR³R⁴— or —SO₂—NR³—, and R¹, R², R³ and R⁴ are each a hydrogen atom or an alkyl group having 1 to 4 carbon atoms, along with following two methods as a method for the preparation of this trifluoromethanesulfonamide derivative. Namely, there are provided a method for the preparation of a trifluoromethanesulfonamide derivative represented by the general formula

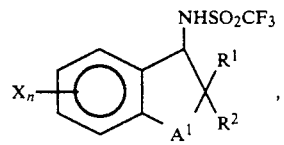

[I-A]

in which X, n, R¹, R² and A¹ each have the same meaning as defined below, i.e. a trifluoromethanesulfonamide derivative having a (thio)chroman ring or a 3,4-dihydro-2H-1,2-benzothiazine 1,1-dioxide ring, characterized by reacting an amine derivative represented by the general formula

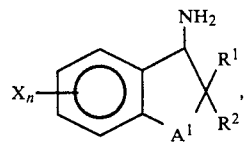

[II]

in which X and n each have the same meaning as defined above and A¹ is —O—CR³R⁴—, —S—CR³R⁴— or —SO₂—NR³—, and R¹, R², R³ and R⁴ each have the same meaning as defined above, and a trifluoromethanesulfonyl halide or trifluoromethanesulfonic anhydride, hereinafter referred to as the Method 1, and a method for the preparation of a trifluoromethanesulfonamide derivative represented by the general formula

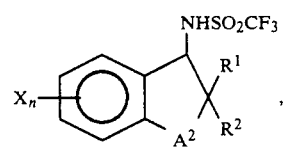

[I-B]

in which X and n each have the same meaning as defined above, A² is —SO—CR³R⁴— or —SO₂—CR³R⁴—, and R¹, R², R³ and R⁴ each have the same meaning as defined above, characterized by oxidizing a trifluoromethanesulfonamide derivative having a thiochroman ring represented by the general formula

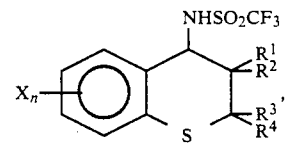

[I-A']

in which X, n, R¹, R², R³ and R⁴ each have the same meaning as defined above, hereinafter referred to as the Method 2.

Further, the present invention provides a herbicide containing the trifluoromethanesulfonamide derivative represented by the general formula [I].

The compound represented by the above given general formula [I] is a trifluoromethanesulfonamide derivative and, in the formula, X, n, R¹, R², R³, R⁴ and A each have the meaning defined above. Namely, X is a hydrogen atom, a halogen atom such as chlorine atom, bromine atom, fluorine atom, iodine atom and the like, an alkyl group having 1 to 4 carbon atoms such as methyl group, ethyl group, propyl group, e.g., n- and isopropyl groups, butyl group, e.g., n-, iso-, sec- and tert-butyl groups, and the like or a haloalkyl group having 1 to 4 carbon atoms such as trifluoromethyl group, trichlcrcmethyl group, dichloroethyl group, tetrafluoroethyl group, monochloromethyl group, monobromomethyl group, monofluoromethyl group, difluoromethyl group, chlorofluoromethyl group, dibromoethyl group, dichloromethyl group, bromofluoromethyl group, heptafluoropropyl group, dibromomethyl group, dibromofluoromethyl group, chlorodifluoromethyl group, bromodifluoromethyl group, dichlorofluoromethyl group, pentafluoroethyl group, difluoroethyl group and the like. And, n is 1, 2 or 3. On the other hand, R¹, R², R³ and R⁴ are each a hydrogen atom or an alkyl group having 1 to 4 carbon atoms such as methyl group, ethyl group, propyl group, e.g., n- and iso-propyl groups, butyl group, e.g., n-, iso-, —S CR³R⁴—, —SO—CR³R⁴—, —SO₂—CR³R⁴— or —SO₂—NR³—.
The trifluoromethanesulfonamide derivatives of the present invention include a variety of compounds and are exemplified, in addition to the compounds obtained in the Preparation Examples described below, by those expressed by the following structural formulas:
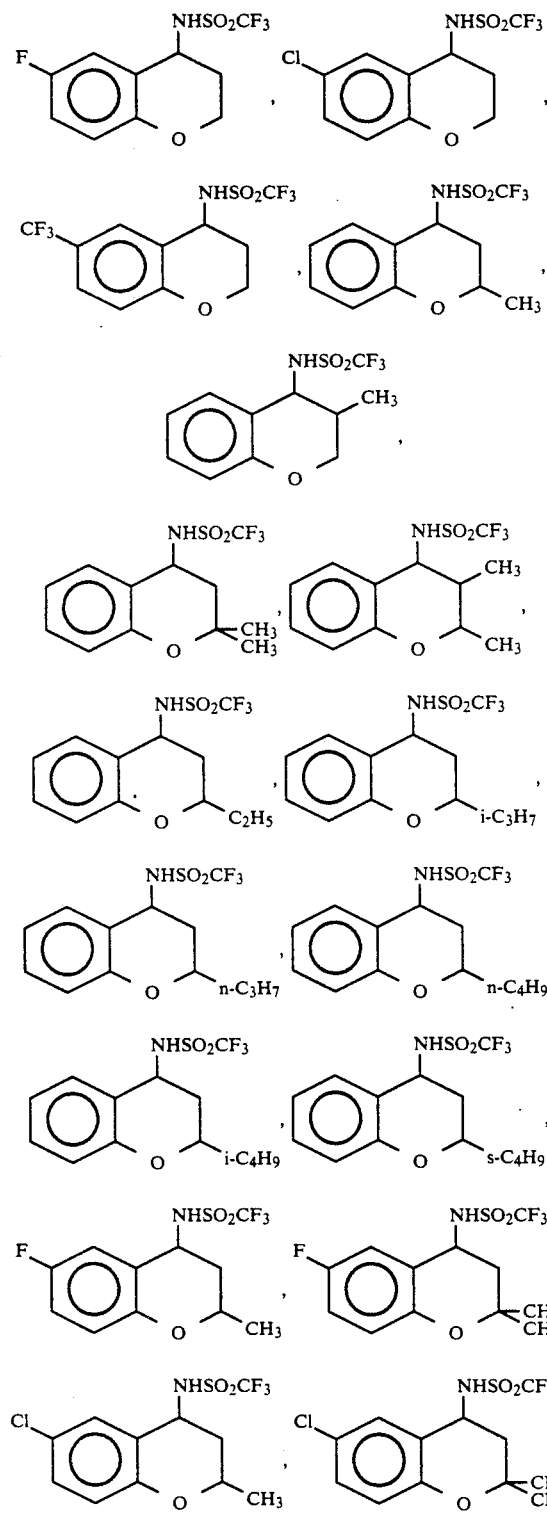
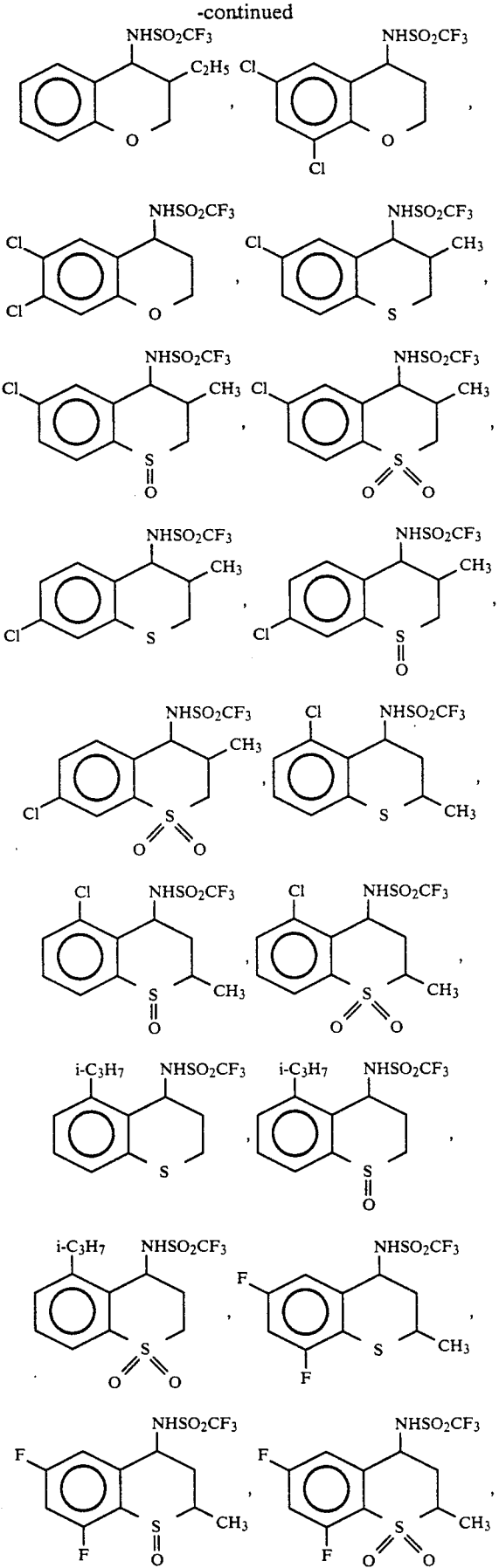

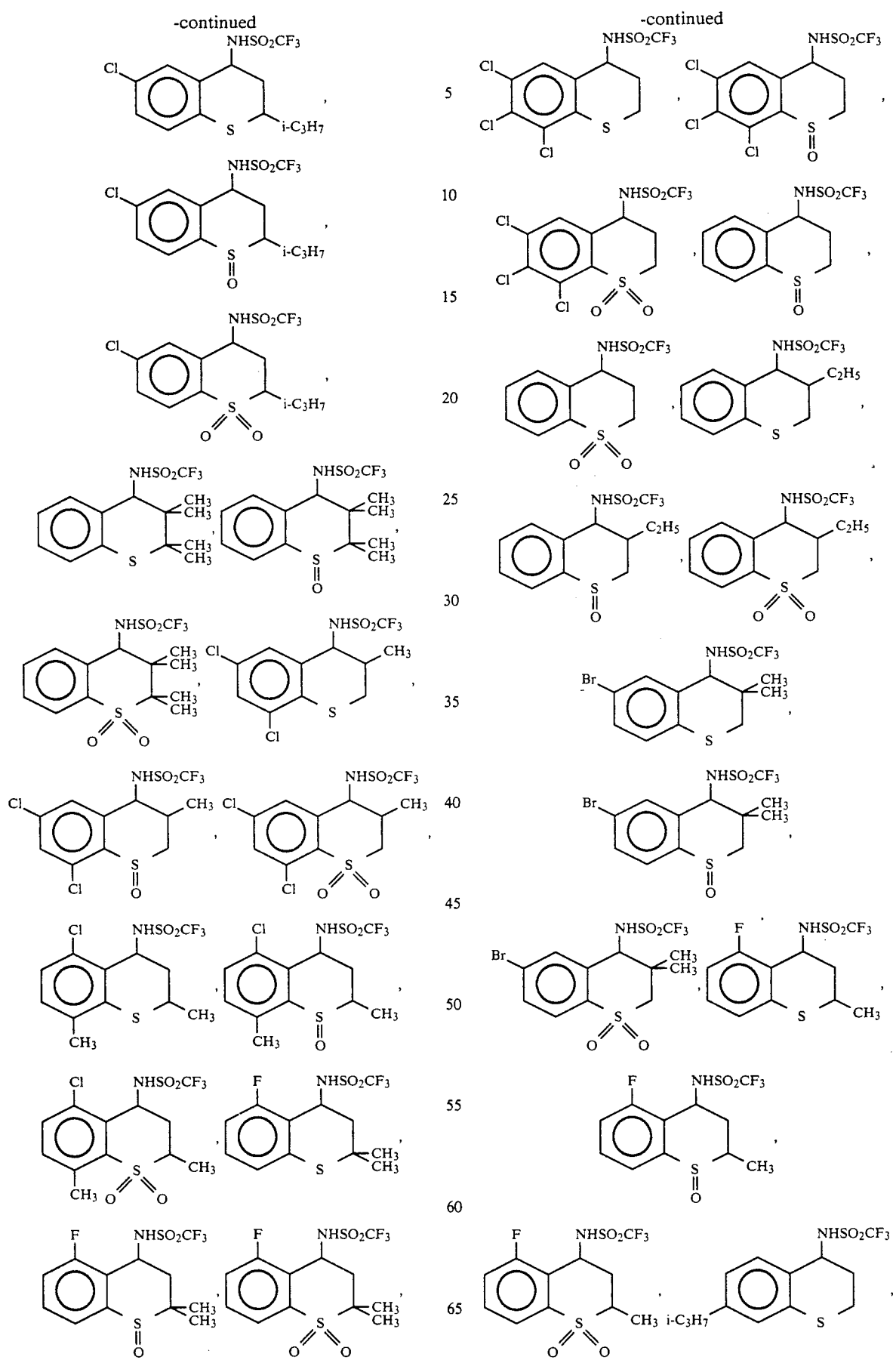

-continued
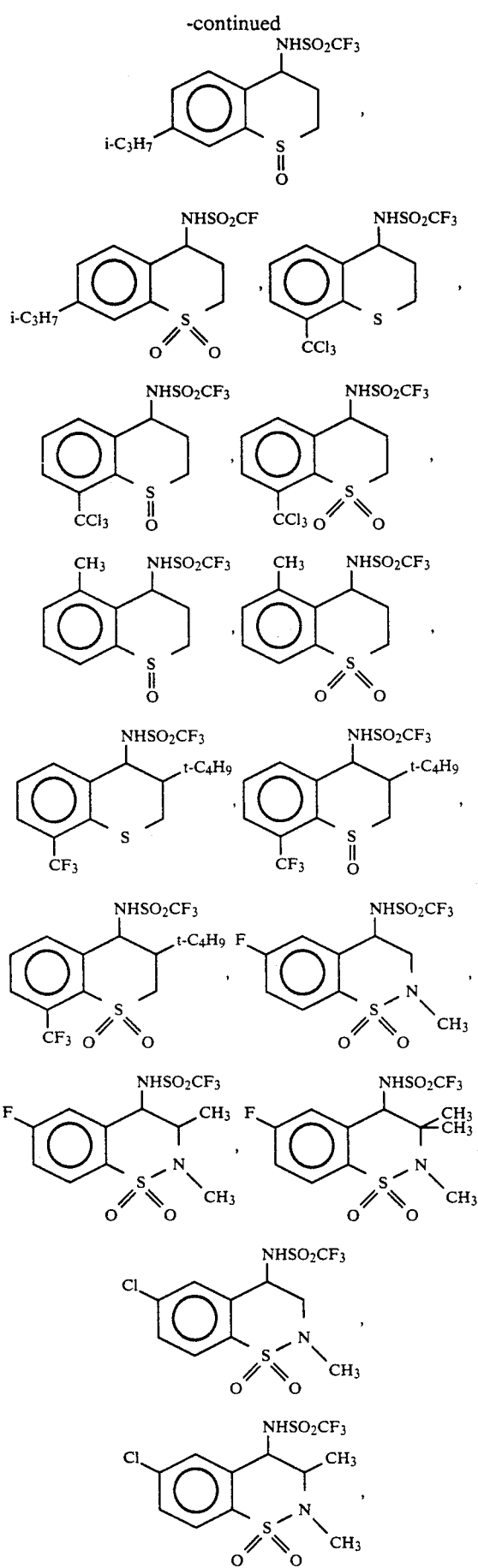
-continued
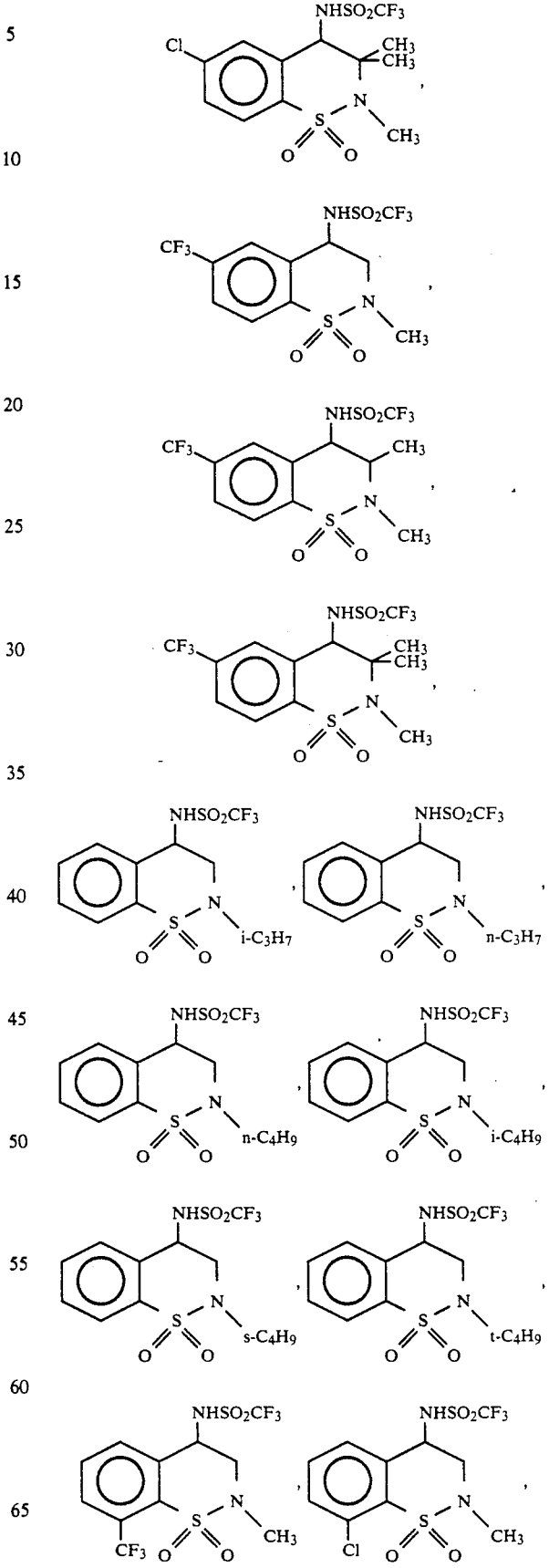

-continued
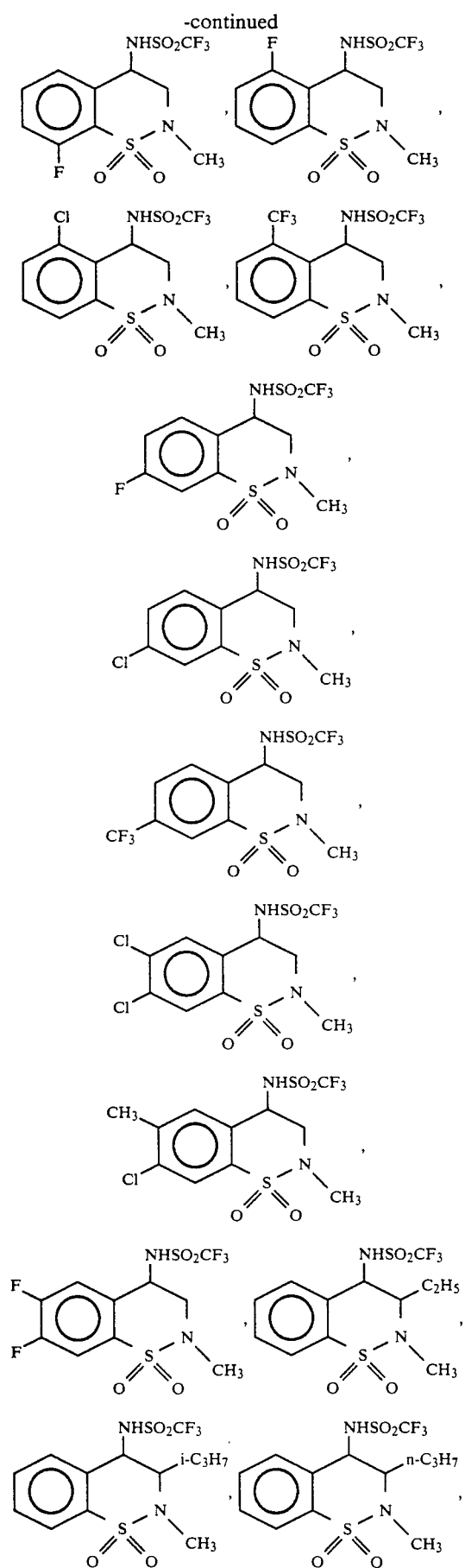
-continued
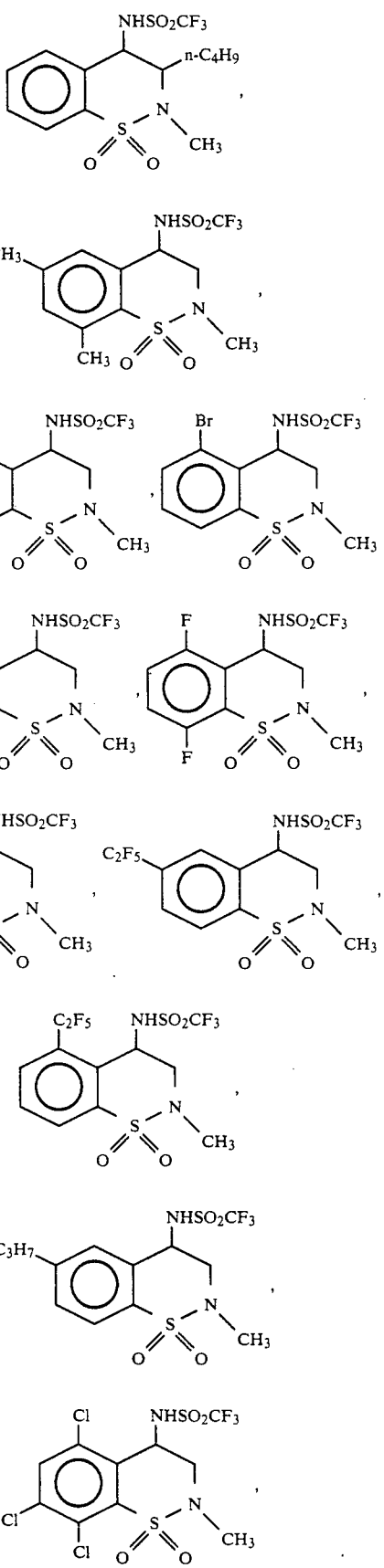

-continued

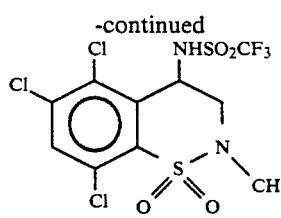

The trifluoromethanesulfonamide derivative represented by the above given general formula [I] can be prepared by a variety of methods. Among them, the above described Method 1 and Method 2 can be named as an efficient method for the preparation.

According to the Method 1, an amine derivative represented by the general formula [II] and a trifluoromethanesulfonyl halide, such as $CF_3SO_2Cl$, $CF_3SO_2Br$, $CF_3SO_2F$ and the like, or trifluoromethanesulfonic anhydride $(CF_3SO_2)_2O$ are reacted to give the desired trifluoromethanesulfonamide derivative represented by the general formula [I-A], i.e., trifluoromethanesulfonamide derivative having a chroman ring, thiochroman ring or 3,4-dihydro-2H-1,2-benzothiazine 1,1-dioxide ring, corresponding to a part of the trifluoromethanesulfonamide derivatives of the general formula [I] having $-O-CR^3R^4-$, $-S-CR^3R^4-$ or $-SO_2-NR^3-$ as the A in the formula [I].

Here, the amine derivative represented by the general formula [II] or, namely, the amine derivative having a (thio)chroman ring or 3,4-dihydro-2H-1,2-benzothiazine 1,1-dioxide ring includes various compounds. X, n, $R^1$, $R^2$, $R^3$, $R^4$ and $A^1$ in the general formula [II] each have the meaning defined above and, in particular, the amine derivative to be selected should have the substituents, i.e. X, n, $R^1$, $R^2$, $R^3$, $R^4$ and $A^l$, corresponding to the substituents of the trifluoromethanesulfonamide derivative of the general formula [I-A] to be prepared.

While various methods may be applicable to the preparation of the amine derivative represented by the above given general formula [II], meanwhile, the process I or II shown below should be undertaken when $A^1$ in the general formula [II] is $-O-CR^3R^4-$ or or $-S-CR^3R^4-$, the process III IV or V should be undertaken when $A^1$ is $-SO_2-NR^3-$ and the process VI should be undertaken when $R^1$ and $R^2$ are the same alkyl groups having 1 to 4 carbon atoms.

PROCESS I

A (thio)phenol compound represented by the general formula

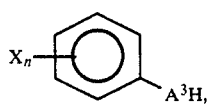

in which X and n each have the same meaning as defined above and $A^3$ is a sulfur atom or oxygen atom, and a halogen-containing ester represented by the general formula

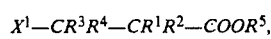

in which $R^1$, $R^2$, $R^3$ and $R^4$ each have the same meaning as defined above, $R^5$ is an alkyl group having 1 to 4 carbon atoms and $X^1$ is a halogen atom, are reacted to produce a phenoxy or phenylthio group-containing ester represented by the general formula

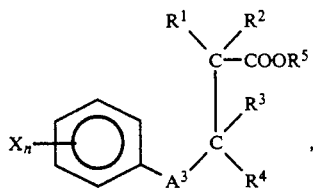

in which X, n, $R^1$, $R^2$, $R^3$, $R^4$, $R^5$ and $A^3$ each have the same meaning as defined above, which is then saponified, i.e., hydrolyzed, to give the phenoxy or phenylthio group-containing carboxylic acid represented by the general formula

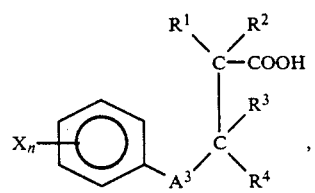

in which X, n, $R^1$, $R^2$, $R^3$, $R^4$ and $A^3$ each have the same meaning as defined above. Meanwhile, the phenoxy or phenylthio group-containing carboxylic acid of this general formula [V'] can be obtained by the reaction of the (thio)phenol compound of the general formula [III] with a halogen-containing carboxylic acid represented by the general formula

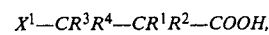

in which $X^1$, $R^1$, $R^2$, $R^3$ and $R^4$ each have the same meaning as defined above.

Further, dehydrative cyclization of the phenoxy or phenylthio group-containing carboxylic acid of the general formula [V'] gives a cyclic keton compound represented by the general formula

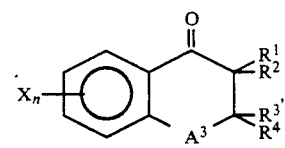

in which X, n, $R^1$, $R^2$, $R^3$, $R^4$ and $A^3$ each have the same meaning as defined above, and the reaction of the same with hydroxylamine or an O-alkyl hydroxylamine represented by the general formula $NH_2OR^6$, in which $R^6$ is a hydrogen atom or an alkyl group having 1 to 4 carbon atoms, gives an oxime or oxime ether compound represented by the general formula

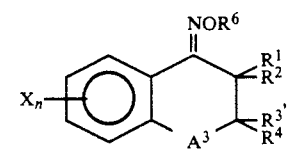

in which X, n, $R^1$, $R^2$, $R^3$, $R^4$, $R^6$ and $A^3$ each have the same meaning as defined above, which is reduced to give an amine derivative with $-O-CR^3R^4-$ or $-S-CR^3R^4-$ as the $A^1$ in the general formula [II].

Meanwhile, reduction of the cyclic ketone compound represented by the general formula [VI] gives a cyclic alcohol compound represented by the general formula

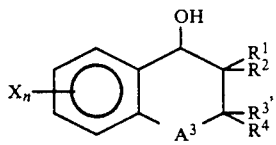  [VIII]

in which X, n, R$^1$, R$^2$, R$^3$, R$^4$ and A$^3$ each have the same meaning as defined above, and the reaction of the same with a halogenating agent such as thionyl chloride and the like gives a halogen-containing compound represented by the general formula

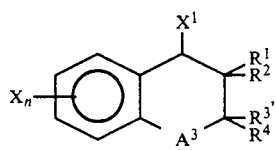  [IX]

in which X, n, X$^1$, R$^1$, R$^2$, R$^3$, R$^4$ and A$^3$ each have the same meaning as defined above, which is reacted with, for example, sodium azide and the like to give an azide compound represented by the general formula

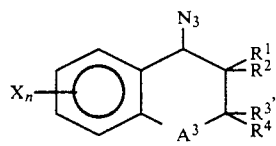  [X]

in which X, n, R$^1$, R$^2$, R$^3$, R$^4$ and A$^3$ each have the same meaning as defined above, which is reduced to give an amine derivative with —O—CR$^3$R$^4$— or —S—CR$^3$-R$^4$— as the A$^1$ in the general formula [II].

PROCESS II

The (thio)phenol compound represented by the general formula [III] is reacted with an unsaturated carboxylic acid ester represented by the general formula

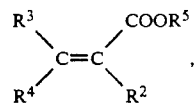  [XI]

in which R$^2$, R$^3$, R$^4$ and R$^5$ each have the same meaning as defined above to give a phenoxy or phenylthio group-containing ester represented by the general formula

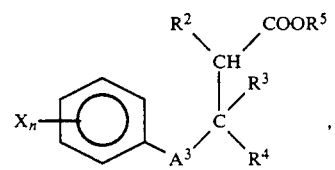  [V-A]

in which X, n, R$^2$, R$^3$, R$^4$, R$^5$ and A$^3$ each have the same meaning as defined above, which is saponified, i.e. hydrolyzed, to give the phenoxy or phenylthio group-containing carboxylic acid represented by the general formula

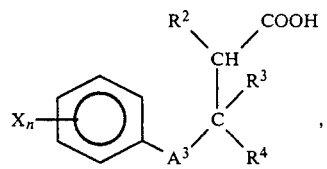  [V'-A]

in which X, n, R$^2$, R$^3$, R$^4$ and A$^3$ each have the same meaning as defined above. Meanwhile, the phenoxy or phenylthio group-containing carboxylic acid of the general formula [V'-A] can be obtained by the reaction of the (thio)phenol compound of the general formula [III] with an unsaturated carboxylic acid represented by the general formula

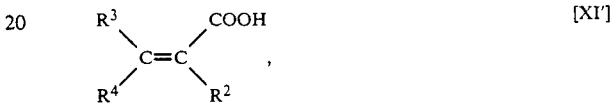  [XI']

in which R$^2$, R$^3$ and R$^4$ each have the same meaning as defined above.

Dehydrative cyclization of the thus obtained phenoxy or phenylthio group-containing carboxylic acid of the general formula [V'-A] gives a cyclic ketone represented by the general formula

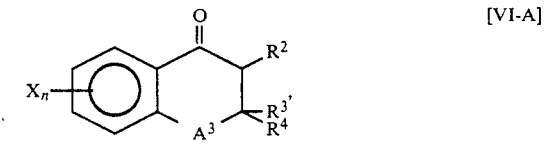  [VI-A]

in which X, n, R$^2$, R$^3$, R$^4$ and A$^3$ each have the same meaning as defined above, namely, with a hydrogen atom as the R$^1$ in the general formula [VI], which is reacted with an alkyl halide represented by the general formula R$^7$X$^1$, in which X$^1$ has the same meaning as defined above and R$^7$ is an alkyl group having 1 to 4 carbon atoms, to give a cyclic ketone compound with an alkyl group having 1 to 4 carbon atoms as the R$^1$ in the general formula [VI]. Meanwhile, a subsequent treatment undertaken in the same manner as in the process I gives an amine derivative with —O—CR$^3$R$^4$— or —S—CR$^3$R$^4$— as the A$^1$ and an alkyl group having 1 to 4 carbon atoms as the R$^1$ in the general formula [II]. Meanwhile, the treatment with the general formula R$^7$X$^1$ is not necessary in the above described process II when an amine derivative with —O—CR$^3$R$^4$— or —S—CR$^3$R$^4$— as the A$^1$ and a hydrogen atom as the R$^1$ in the general formula [II] is desired.

PROCESS III

This method is a method described in Journal of Organic Chemistry, volume 30, page 2241 (1965) and volume 31, page 162 (1966).

A saccharin compound represented by the general formula

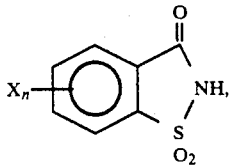
[XII]

in which X and n each have the same meaning as defined above, is reacted with a halogenated acetone represented by the general formula $X^1$—$CH_2$—CO—$CH_3$, in which $X^1$ has the same meaning as defined above, in the presence of a suitable base such as sodium hydride, sodium hydroxide, sodium carbonate and the like to give an N-acetonyl saccharin compound represented by the general formula

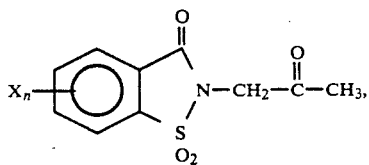
[XII']

in which X and n each have the same meaning as defined above.

In the next place, the N-acetonyl saccharin compound represented by the general formula [XII'] is reacted with at least 2 equivalent of sodium ethoxide to give a 3-acetyl-2H-1,2-benzothiazin-4(3H)-one 1,1-dioxide compound as a cyclic ketone compound represented by the general formula

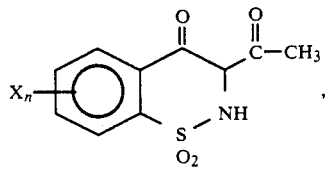
[XII'']

in which X and n each have the same meaning as defined above.

The 3-acetyl-2H-1,2-benzothiazin-4(3H)-one 1,1-dioxide compound represented by this general formula [XII''] is reacted with 3 to 10 equivalent of ethylene glycol under reflux of benzene to give a ketalized cyclic ketone compound, i.e. 2H-1,2-benzothiazin-4(3H)-one 1,1-dioxide compound represented by the general formula

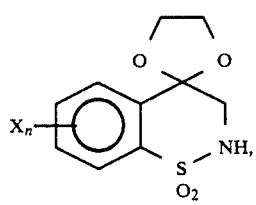
[XII''']

in which X and n each have the same meaning as defined above. Further, the ketalized 2H-1,2-benzothiazin-4(3H)-one 1,1-dioxide compound represented by the general formula [XII'''] is reacted with an alkyl halide represented by the general formula $R^8X^1$, in which $X^1$ has the same meaning as defined above and $R^8$ is an alkyl group having 1 to 4 carbon atoms, in the presence of a suitable acid acceptor such as triethylamine, di-methylaniline, pyridine and the like for N-alkylation followed by hydrolysis under an acidic condition to give an N-alkylated cyclic ketone compound, i.e., 2H-1,2-benzothiazin-4(3H)-one 1,1-dioxide compound, represented by the general formula

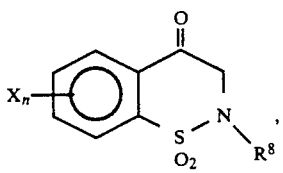
[VI-B]

in which X, n and $R^3$ each have the same meaning as defined above. The same treatment as in the process I subsequently undertaken gives an amine derivative with —$SO_2$ $NR^3$— as the $A^1$, hydrogen atoms as the $R^1$ and $R^2$ and alkyl group having 1 to 4 carbon atoms as the $R^3$ in the general formula [II]. Meanwhile, the treatment with the general formula $R^8X^1$ is not necessary in the above described process III when an amine derivative with —$SO_2$—$NR^3$— as the $A^1$ and a hydrogen atom as the $R^3$ also in the general formula [II] is desired.

PROCESS IV

This method is a method described in Journal of the Chemical Society, Perkin I, page 2589 (1974) and Journal of Chemical Communication, page 771 (1976).

A saccharin compound represented by the general formula [XII] is reacted with 2 equivalents of a suitable organometallic compound such as methyllithium, methylmagnesium iodide and the like to give a 3-methyl-1,2-benzoisothiazo-e 1,1-dioxide compound represented by the general formula

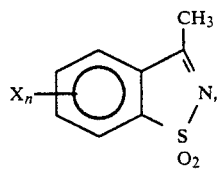
[XIII]

in which X and n each have the same meaning as defined above.

In the next place, the 3-methyl-1,2-benzoisothiazole 1,1-dioxide compound represented by the general formula [XIII] is reacted with 1 equivalent of bromine to give a 3-bromomethyl-1,2-benzoisothiazole 1,1-dioxide compound represented by the general formula

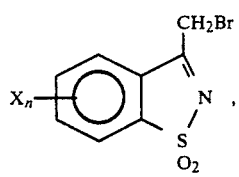
[XIII']

in which X and n each have the same meaning as defined above.

Further, the 3-bromomethyl-1,2-benzoisothiazole 1,1-dioxide compound represented by the general formula [XIII'] is reacted with at least 2 equivalents of sodium ethoxide to give a cyclic ketone compound, i.e., 2H-1,2-benzothiazin-4(3H)-one 1,1-dioxide compound, represented by the general formula

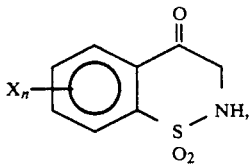

in which X and n each have the same meaning as defined above. The same treatment as in the process I subsequently undertaken gives an amine derivative with —SO$_2$—NR$^3$— as the A$^1$ and hydrogen atoms as the R$^1$, R$^2$ and R$^3$ in the general formula [II].

Meanwhile, the saccharin compound represented by the general formula [XII] and used as the starting material in the processes III and IV can be prepared in a variety of methods and, for example, can be prepared by the method shown below as disclosed in Journal of Organic Chemistry, volume 36, page 1843 (1971).

A benzenesulfonyl halide compound represented by the general formula

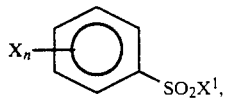

in which X, n and X$^1$ each have the same meaning as defined above, is reacted with tert-butylamine in the presence of a suitable acid acceptor such as triethylamine, diethylaniline, pyridine and the like to give an N-tert-butylbenzenesulfonamide compound represented by the general formula

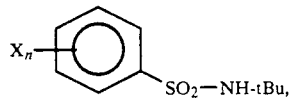

in which X and n each have the same meaning as defined above. In this case, the acid acceptor is not indispensable and the tert-butylamine may serve as an acid acceptor when used in an excessive amount.

In the next place, the N-tert-butylbenzenesulfonamide compound represented by the general formula [XIV'] is converted into a metal salt by use of at least two equivalent of an organometallic compound such as n-butyllithium and the like and this is reacted with carbon dioxide gas to give a 2-(N-tert-butylsulfamoyl) benzoic acid compound represented by the general formula

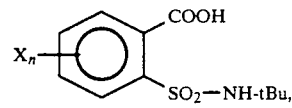

in which X and n each have the same meaning as defined above. Further, the saccharin compound represented by the general formula [XII] can be obtained by heating this 2-(N-tert-butylsulfamoyl) benzoic acid compound represented by the general formula [XIV"] in polyphosphoric acid.

PROCESS V

When the 2H-1,2-benzothiazin-4(3H)-one 1,1-dioxide compounds represented by the general formulas [VI-B] and [VI-C] prepared in the processes III and IV, referred to as the cyclic ketone compounds 1, are reacted in the presence of a suitable base such as sodium hydride, sodium amide, sodium ethoxide and the like with a suitable alkoxycarbonylating agent such as ethyl chloroformate, methyl chloroformate, ethyl carbonate and the like represented by the general formula X$^2$COOR, in which X$^2$ is a halogen atom or an alkoxy group having 1 to 3 carbon atoms and R is an alkyl group having 1 to 3 carbon atoms, a 3-alkoxycarbonyl-2H-1,2-benzothiazin-4(3H)-one 1,1-dioxide compound represented by the general formula

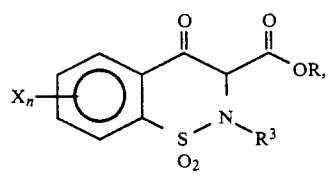

in which X, n, R and R$^3$ each have the same meaning as defined above, referred to as the cyclic ketone compound 2, is obtained.

In the next place, this 3-alkoxycarbonyl-2H-1,2-benzothiazin-4(3H)-one 1,1-dioxide compound represented formula [XV] is reacted in the presence of a suitable base such as sodium hydride, triethylamine, sodium carbonate and the like with an alkyl halide represented by the general formula R$^9$X$^1$, in which R$^9$ is an alkyl group having 1 to 4 carbon atoms and X$^1$ has the same meaning as defined above, to give a 3-alkyl-3-alkoxycarbonyl-2H-1,2-benzothiazin-4(3H)-one 1,1-dioxide compound represented by the general formula

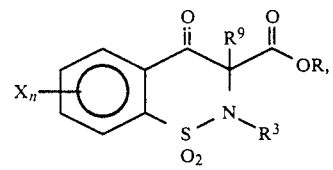

in which X, n, R, R$^9$ and R$^3$ each have the same meaning as define above, which is referred to as the cyclic ketone compound 3.

In the next place, this 3-alkyl-3-alkoxycarbonyl-2H-1,2-benzothiazin-4(3H)-one 1,1-dioxide compound represented by the general formula [XV'] is heated under a basic condition or under an acidic condition to effect hydrolysis and decarboxylation reaction to give a 3-alkyl-2H-1,2-benzothiazin-4(3H)one 1,1-dioxide compound represented by the general formula

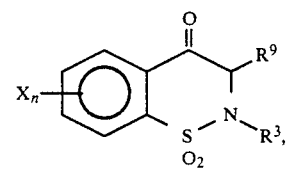

in which X, n, R$^3$ and R$^9$ each have the same meaning as defined above, which is referred to as the cyclic ketone compound 4.

Further, this 3-alkyl-2H-1,2-benzothiazin-4(3H)-one 1,1-dioxide compound represented by the general formula [XV"] is reacted in the presence of a suitable base such as sodium hydride, sodium amide, sodium ethoxide and the like with an alkyl halide represented by the general formula $R^{10}X^1$, in which $X^1$ has the same meaning and $R^{10}$ is an alkyl group having 1 to 4 carbon atoms, to give a 3,3-dialkyl-2H-1,2-benzothiazin-4(3H)-one 1,1-dioxide compound represented by the general formula

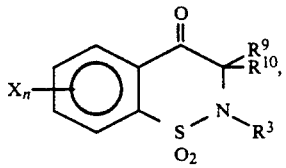

[VI-D]

in which X, n, $R^9$, $R^{10}$ and $R^3$ each have the same meaning as defined above, which is referred to as the cyclic ketone compound 5, followed by the same treatment as in the process I subsequently undertaken to give an amine derivative with $—SO_2—NR^3—$ as the $A^1$ and alkyl groups having 1 to 4 carbon atoms as the $R^1$ and $R^2$ in the general formula [II]. Meanwhile, it is not necessary in order to prepare an amine derivative with a hydrogen atom as the $R^2$ and $—SO_2—NR^3—$ as the $A^1$ in the general formula [II] to undertake the reaction of the 3-alkyl-2H-1,2-benzothiazin-4(3H)-one 1,1-dioxide compound represented by the general formula [XV''] with the alkyl halide represented by the general formula $R^{10}X^1$ in the presence of a base. Besides, an amine derivative with $—SO_2—NR^3—$ as the $A^1$ and a hydrogen atom as the $R^3$ in the general formula [II] can be prepared by using a 2H-1,2-benzothiazin-4(3H)-one 1,1-dioxide compound represented by the general formula [VI-C] with hydrogen as the $R^3$ as the starting material. Further, an amine derivative with $—SO_2—NR^3—$ as the $A^1$ and an alkyl group having 1 to 4 carbon atoms as the $R^3$ in the general formula [II] can be prepared by using a 2H-1,2-benzothiazin-4(3H)-one 1,1-dioxide compound represented by the general formula [VI-B] with an alkyl group having 1 to 4 carbon atoms as the $R^3$ as the starting material.

PROCESS VI

An amine derivative with the same alkyl groups having 1 to 4 carbon atom as the $R^1$ and $R^2$ in the general formula II] or, namely, an amine derivative represented by the general formula

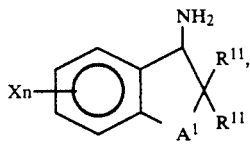

[II-A]

in which X, n and $A^1$ each have the same meaning as defined above and $R^{11}$ is an alkyl group having 1 to 4 carbon atoms, can be obtained by using a cyclic ketone compound obtained by the process I, II, III or IV with hydrogen atoms as the $R^1$ and $R^2$ or, namely, a cyclic ketone compound represented by the general formula

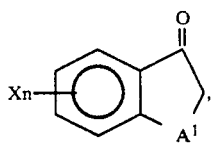

[VI-E]

in which X, n and $A^1$ each have the same meaning as defined above, as the starting material and converting the same by the reaction with an alkyl halide represented by the general formula $R^{11}X^1$, in which $R^{11}$ and $X^1$ each have the same meaning as defined above, into a cyclic ketone compound represented by the general formula

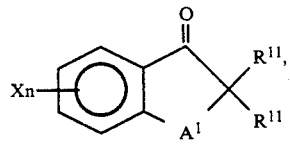

[VI—F]

in which X, n, $R^{11}$ and $A^1$ each have the same meaning as defined above, followed by the same treatment as in the process I subsequently undertaken to give the amine derivative of the general formula [II-A].

In the Method 1 of the present invention, the amine derivative obtained by above mentioned procedure represented by the general formula [II], which also includes the general formula [II-A], and a trifluoromethanesulfonyl halide or trifluoromethanesulfonic anhydride are reacted and the conditions in this case are not particularly limitative. Usually, the reaction may be performed by using a suitable solvent such as tetrahydrofuran, dimethoxyethane, benzene, toluene, xylene, methylene chloride, chloroform, dimethylformamide, dimethyl sulfoxide and the like in the presence of an acid acceptor such as triethylamine, dimethylaniline, pyridine and the like at a temperature of $-15°$ C. to $80°$ C. for about 30 minutes to several hours. Incidentally, this reaction can proceed also without any solvent.

In the Method 2 of the present invention, in the next place, the thiochroman ring-containing trifluoromethanesulfonamide derivative represented by the general formula [I-A′] and obtained by the above described Method 1 or other methods, which corresponds to $—S—CR^3R^4—$ as the $A^1$ in the general formula [I-A], is oxidized to give a trifluoromethanesulfonamide derivative as desired represented by the general formula [I-B], which corresponds to a part of the trifluoromethanesulfonamide derivatives of the general formula [I] or, in other words, corresponds to $—SO—CR^3R^4—$ or $—SO_2—CR^3R^4—$ as the A in the formula [I]. The oxidizing agents used here for oxidizing the thiochroman ring-containing trifluoromethanesulfonamide derivative of the general formula [I-A′] include various ones, of which, for example, oxidizing agents such as hydrogen peroxide, sodium metaperiodate, peracetic acid, perbenzoic acid, m-chloroperbenzoic acid, chromic acid, potassium permanganate and the like are preferred. The conditions of this oxidation reaction are not particularly limitative and may be appropriately selected depending on the situation but, usually, the reaction can be performed by using a solvent such as acetic acid, acetone, methyl alcohol, tertbutyl alcohol and the like at a reaction temperature of $0°$ to $150°$ C. for about 1 to 20 hours. When the $A^2$ in the trifluoromethanesulfonamide derivative of the general formula [I-B] as the desired product is $—SO—CR^3R^4—$, it is preferable that the reaction is conducted by adding about 1 mole of the oxidizing agent and, when $A^2$ is $—SO_2—CR^3R^4—$, by adding at least 2 moles of the oxidizing agent per mole of the thiochroman ring-containing trifluoromethanesulfonamide derivative of the general formula [I-A′].

In the above described Method 1 and Method 2 of the present invention, the product is, after completion of the above described reaction, isolated and washed to give the trifluoromethanesulfonamide derivative of the present invention represented by the general formula [I], i.e. general formulas [I-A] and [I-B], in a high purity and in a high yield.

The trifluoromethanesulfonamide derivative of the present invention prepared in this manner is a novel compound and particularly effective as a herbicide and also can be utilized as a plant growth regulator.

To follow up, the herbicide of the present invention contains the above described trifluoromethanesulfonamide derivative represented by the general formula [I] or, in particular, contains the same as the active ingredient. This herbicide can be applied in a preparation form such as wettable powder, emulsifiable concentrate, dust, granules and the like by blending the above described derivative as the active ingredient with a liquid carrier such as an organic solvent and the like or a solid carrier such as a fine mineral powder and the like. A surface active agent may be added in the preparation form in order to impart emulsifiability, dispersibility, spreadability and the like.

When the herbicide of the present invention is used in the form of wettable powder, it is usual to use a composition prepared by compounding the compound of the present invention represented by the above given general formula [I] as the active ingredient in a proportion of 10 to 55% by weight, a solid carrier in a proportion of 40 to 88% by weight and a surface active agent in a proportion of 2 to 5% by weight. And, when used in the form of emulsifiable concentrate, it is usual to prepare the same by compounding the compound of the present invention as the active ingredient in a proportion of 20 to 50% by weight, a solvent in a proportion of 35 to 75% by weight and a surface active agent in a proportion of 5 to 15% by weight. When used in the form of dust, on the other hand, it is usual to prepare the same by compounding the compound of the present invention represented by the general formula [I] as the active ingredient in a proportion of 1 to 15% by weight, a solid carrier in a proportion of 80 to 97% by weight and a surface active agent in a proportion of 2 to 5% by weight. Further, when used in the form of granules, it is prepared by compounding the compound of the present invention represented by the general formula [I] as the active ingredient in a proportion of 3 to 15% by weight, a solid carrier in a proportion of 80 to 95% by weight and a surface active agent in a proportion of 2 to 5% by weight.

Fine mineral powder is used here as the solid carrier and the fine mineral powder is exemplified by oxides such as diatomaceous earth, slaked lime and the like, phosphates such as apatite and the like, sulfates such as gypsum and the like, silicates such as talc, pyrophyllite, clay, kaolin, bentonite, acid clay, white carbon, quartz powder, silica stone powder and the like, and so on.

And, organic solvents are used as the solvent and particular examples thereof include aromatic hydrocarbons such as xylene, toluene, benzene and the like, chlorinated hydrocarbons such as o-chlorotoluene, trichloroethane, trichloroethylene and the like, alcohols such as cyclohexanol, amyl alcohol, ethylene glycol and the like, ketones such as isophorone, cyclohexanone, cyclohexenylcyclohexanone and the like, ethers such as butyl cellosolve, dimethyl ether, methyl ethyl ether and the like, esters such as isopropyl acetate, benzyl acetate, methyl phthalate and the like and amides such as dimethylformamide and the like as well as mixtures thereof.

Further, as surface active agents, any of anionic, nonionic and cationic surface active agents, and amphoteric surface active agents (e.g., amino acid and betaine) can be used.

Incidentally, it is optional to use other herbicidal ingredients as the active ingredients of the herbicide of the present invention in combination with the trifluoromethanesulfonamide derivative represented by the general formula [I]. Hitherto marketed herbicides are named as there additional herbicidal ingredients and there can be named various ones such as phenoxy herbicides, diphenyl ether herbicides, triazine herbicides, urea herbicides, carbamate herbicides, thiol carbamate herbicides, acid anilide herbicides, uracil herbicides, pyridinium salt herbicides, phosphorus herbicides, toluidine herbicides and the like.

Further, it is optional according to need to use the herbicide of the present invention as admixed with insecticides, fungicides, plant growth regulators, fertilizers and the like.

PREPARATION EXAMPLE 1

5.07 g (0.034 mole) of 4-aminochroman and 4.0 g (0.04 mole) of triethylamine were dissolved in 50 ml of methylene chloride and cooled to 5° C. in an ice bath. This was admixed with 11.3 g (0.04 mole) of trifluoromethanesulfonic anhydride in such a manner that the temperature did not exceed 10° C. Thereafter, reaction was performed at room temperature for 2 hours and the reaction mixture was washed with 5% hydrochloric acid and then with water and dried over anhydrous sodium sulfate followed by concentration under reduced pressure The thus obtained oily material was dissolved in 85 ml of ethyl alcohol containing 8.9 g of potassium hydroxide and, aiter standing overnight, poured into water and washed with ether. Further, it was made acidic with 5% hydrochloric acid and the crystals formed were collected by filtration. As a result, the compound 1 was obtained. The structural formula as well as the analytical results and the like are shown in Tables 1 and 2.

PREPARATION EXAMPLES 2 TO 6

The compounds 2 to 6 were obtained by undertaking the same procedure as in Preparation Example 1 except 4-aminothiochroman (Preparation Example 2), 4-amino-7-chloro thiochroman (Preparation Example 3), 4-amino-5-methylthiochroman (Preparation Example 4), 4-amino-5,8-dichlorothiochroman (Preparation Example 5) or 4-amino-8-trifluoromethylthiochroman (Preparation Example 6) were used in place of the 4-aminochroman in Preparation Example 1. The structural formulas and the analytical results thereof are shown in Tables 1 and 2.

PREPARATION EXAMPLES 7 AND 8

The same procedure as in Preparation Example 1 was undertaken to give 6.8 g of a solid excepting the use of 4-amino-3-methylthiochroman in place of the 4-aminochroman in Preparation Example 1. This solid exhibited two spots on a thin-layer chromatogram so that it was adsorbed on a silica gel and eluted out by using a solvent mixture of equal amounts of methylene chloride and n-hexane. As a result, the compound 7 and compound 8 were obtained. The structural formulas and the analytical results thereof are shown in Tables 1 and 2.

The results of the analysis indicated that the compound 7 was cis-3-methyl-4-trifluoromethanesulfonaminothiochroman and the compound 8 was trans-3-methyl-4-trifluoromethanesulfonaminothiochroman.

PREPARATION EXAMPLES 9 AND 10

The same procedure as in Preparation Example 1 was undertaken to give 7.7 g of a solid except 4-amino-6-fluoro-2-methylthiochroman were used in place of the 4-aminochroman in Preparation Example 1. This solid exhibited two spots on a thin-layer chromatogram so that it was adsorbed on a silica gel and eluted out by using a solvent mixture of equal amounts of methylene chloride and n-hexane As a result, the compound 9 and compound 10 were obtained. The structural formulas and the analytical results thereof are shown in Tables 1 and 2.

The results of the analysis indicated that the compound 9 was 6-fluoro-trans-2-methyl-4-trifluoromethanesulfonaminothiochroman and the compound 10 was 6-fluoro-cis-2-methyl-4-trifluoromethanesulfonaminothiochroman.

PREPARATION EXAMPLES 11 AND 12

The same procedure as in Preparation Example 1 was undertaken to obtain the compound 11 or compound 12 except 4-amino-8-chloro-3-methylthiochroman (Preparation Example 11) or 4-amino-6,7-dichloro-2-methyl-thiochroman (Preparation Example 12) were used in place of the 4-aminochroman in Preparation Example 1. The structural formulas and the analytical results thereof are shown in Tatles 1 and 2.

The results of the analysis indicated that the compound 11 was 8-chloro-cis-3-methyl-4-trifluoromethanesulfonaminothiochroman and the compound 12 was 6,7-dichloro-trans-2-methyl-4-trifluoromethanesulfonaminothiochroman.

PREPARATION EXAMPLES 13 AND 14

The same procedure as in Preparation Example 1 was undertaken to obtain 7.3 g of a solid except 4-amino-2-n-propylthiochroman were used in place of the 4-aminochroman in Preparation Example 1. This solid exhibited two spots on a thin-layer chromatogram so that it was adsorbed on a silica gel and eluted out by using a 1:5 solvent mixture of ethyl acetate and n-hexane. As a result, the compound 13 and compound 14 were obtained. The structural formulas and the analytical results thereof are shown in Tables 1 and 2.

The results of the analysis indicated that the compound 13 was cis-2-n-propyl-4-trifluoromethanesulfonaminothiochroman and the compound 14 was trans-2-n-propyl-4-trifluoromethanesulfonaminothiochroman.

PREPARATION EXAMPLES 15 AND 16

The same procedure as in Preparation Example 1 was undertaken to obtain 7.0 g of a solid excepting the use of 4-amino-2-ethylthiochroman were used in place of the 4-amino chroman in Preparation Example 1. This solid exhibited two spots on a thin-layer chromatogram so that it was adsorbed on a silica gel and eluted out by using a 1:10 solvent mixture of ethyl acetate and n-hexane. As a result, the compound 15 and compound 16 were obtained. The structural formulas and the analytical results thereof are shown in Tables 1 and 2.

The results of the analysis indicated that the compound 15 was cis-2-ethyl-4-trifluoromethanesulfonaminothiochroman and the compound 16 was trans-2-ethyl-4-trifluoromethanesulfonaminothiochroman.

PREPARATION EXAMPLE 17

0.40 g (1.2 m moles) of the compound 9 obtained in Preparation Example 9 was dissolved in 5.0 ml of acetic acid and 2.0 g (0.018 mole) of 30% aqueous solution of hydrogen peroxide were added thereto. After a reaction for 5 hours at 100° C., it was poured into 50 ml of water and the crystals formed there were collected by filtration. As a result, the compound 17 was obtained. The structural formula and the analytical results thereof are shown in Tables 1 and 2.

The results of the analysis indicated that the compound 17 was 6-fluoro-trans-2-methyl-4-trifluoromethanesulfone-aminothiochroman-1,1-dioxide.

PREPARATION EXAMPLES 18 TO 20

The same procedure as in Preparation Example 17 was undertaken to obtain the compound 18, compound 19 or compound 20 except the compound 10 (Preparation Example 18), compound 15 (Preparation Example 19) or compound 16 (Preparation Example 20) were used in place of the compound 9 in Preparation Example 17. The structural formulas and the analytical results thereof are shown in Tables 1 and 2.

The results of the analysis indicated that the compound 18 was 6-fluoro-cis-2-methyl-4-trifluoromethanesulfoaminothio-chroman-1,1-dioxide, the compound 19 was cis-2-ethyl-4-trifluoromethanesulfoaminothiochroman-1,1-dioxide and the compound 20 was trans-2-ethyl-4-trifluoromethanesulfoaminothiochroman-1,1-dioxide.

PREPARATION EXAMPLES 21 AND 22

The same procedure as in Preparation Example 1 was undertaken except 4-amino-6-fluorothicchroman (Preparation Example 21) or 4-amino-6-fluoro-2,2-dimethyl-thiochroman (Preparation Example 22) were used in place of the 4-aminochroman in Preparation Example 1 and the thus obtained compounds were used in place of the compound 9 in Preparation Example 17 in the same procedure as in Preparation Example 17 to obtain the compound 21 or compound 22. The structural formulas and the analytical results thereof are shown in Tables 1 and 2.

PREPARATION EXAMPLE 23

1.0 g (3 m moles) of the compound 9 obtained in Preparation Example 9 was dissolved in 10 ml of acetic acid and 0.34 g (3 m moles) of 30% aqueous solution of hydrogen peroxide was added thereto. After a reaction for 24 hours at room temperature, the solvent was distilled off under reduced pressure and the thus obtained solid was adsorbed on a silica gel and eluted out by using a 2:1 solvent mixture of ethyl acetate and n-hexane. In this manner, 0.80 g of the compound 23 was obtained. The structural formula and the analytical results thereof are shown in Tables 1 and 2.

PREPARATION EXAMPLE 24

0.40 g (1.2 m moles) of the compound 13 obtained in Preparation Example 13 was dissolved in 5.0 ml of acetic acid and 0.136 g (1.2 m moles) of 30% aqueous solution of hydrogen peroxide was added thereto. After a reaction for 24 hours at room temperature, the solvent was distilled off under reduced pressure and the thus obtained solid was recrystallized from acetic acid. In this manner, 0.20 g of the compound 24 was obtained. The structural formula and the analytical results thereof are shown in Tables 1 and 2.

PREPARATION EXAMPLES 25 and 26

The same procedure as in Preparation Example 1 was undertaken to give the compound 25 and compound 26 except 3,4-dihydro-2-methyl-4-amino-2H-1,2-benzothiazine 1,1-dioxide (Preparation Example 25) or 3,4-dihydro-2-ethyl-4-amino-2H-1,2benzothiazine 1,1-dioxide (Preparation Example 26) were used in place of the 4-aminochroman in Preparation Example 1. The structural formulas and the analytical results thereof are shown in Tables 1 and 2.

TABLE 1

| Compound No. | Structural formula | Elementary analysis *(%) C | H | N | Melting point (°C.) | Amount obtained (g) | Yield (%) |
|---|---|---|---|---|---|---|---|
| 1 | [chroman with NHSO$_2$CF$_3$] | 42.3 (42.7) | 3.3 (3.6) | 5.1 (5.0) | 78.4~80.3 | 6.8 | 71 |
| 2 | [thiochroman with NHSO$_2$CF$_3$] | 40.6 (40.4) | 3.4 (3.4) | 4.8 (4.7) | 65.5~68.0 | 8.1 | 80 |
| 3 | [Cl-thiochroman with NHSO$_2$CF$_3$] | 37.3 (36.2) | 2.9 (2.7) | 4.0 (4.2) | 111.9~114.5 | 7.3 | 65 |
| 4 | [CH$_3$-thiochroman with NHSO$_2$CF$_3$] | 42.4 (42.4) | 3.7 (3.9) | 4.7 (4.5) | 85.1~87.6 | 6.9 | 65 |
| 5 | [diCl-thiochroman with NHSO$_2$CF$_3$] | 33.0 (32.8) | 2.0 (2.2) | 3.5 (3.8) | 107.4~109.8 | 10.1 | 81 |
| 6 | [CF$_3$-thiochroman with NHSO$_2$CF$_3$] | 36.5 (36.2) | 2.3 (2.5) | 4.3 (3.8) | 78.6~81.0 | 9.5 | 76 |
| 7 | [CH$_3$-thiochroman with NHSO$_2$CF$_3$ cis] | 42.4 (42.4) | 3.7 (3.9) | 4.7 (4.5) | 103.5~105.0 | 4.3 | 41 |
| 8 | [CH$_3$-thiochroman with NHSO$_2$CF$_3$ trans] | 42.4 (42.4) | 3.7 (3.9) | 4.9 (4.5) | 63.0~65.0 | 2.1 | 20 |

TABLE 1-continued
| Compound No. | Structural formula | Elementary analysis *(%) C | H | N | Melting point (°C.) | Amount obtained (g) | Yield (%) |
|---|---|---|---|---|---|---|---|
| 9 | 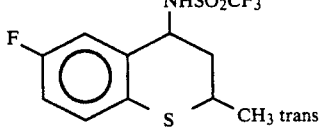 | 39.8 (40.1) | 3.1 (3.4) | 4.1 (4.1) | 101.8~104.1 | 3.4 | 29 |
| 10 | 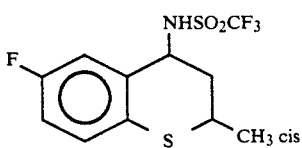 | 39.6 (40.1) | 3.0 (3.4) | 3.9 (4.3) | 136.0~136.6 | 2.3 | 21 |
| 11 | 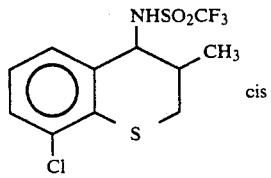 | 38.7 (38.2) | 3.1 (3.2) | 3.8 (4.1) | 114.5~115.5 | 8.5 | 72 |
| 12 | 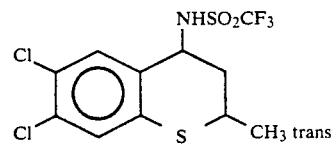 | 35.6 (34.7) | 2.7 (2.7) | 3.6 (3.7) | 144.1~146.3 | 8.0 | 62 |
| 13 | 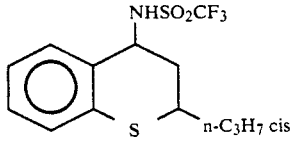 | 45.7 (46.0) | 4.6 (4.8) | 4.3 (4.1) | 147.1~148.8 | 3.7 | 32 |
| 14 | 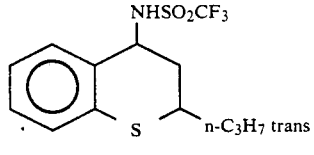 | 45.7 (46.0) | 4.7 (4.8) | 4.3 (4.1) | 108.5~109.4 | 1.2 | 10 |
| 15 | 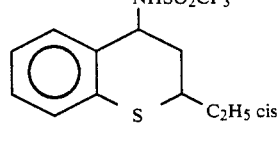 | 44.3 (44.3) | 4.3 (4.3) | 4.4 (4.3) | 138.8~140.4 | 2.9 | 26 |
| 16 | 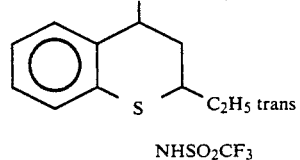 | 44.4 (44.3) | 4.4 (4.3) | 4.5 (4.3) | 98.4~100.5 | 1.4 | 12 |
| 17 | 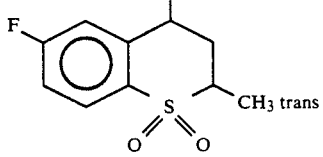 | 36.0 (36.6) | 2.8 (3.1) | 3.6 (3.9) | 132.7~133.6 | 0.37 | 83 |
| 18 | 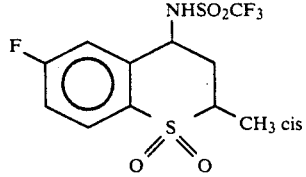 | 36.1 (36.6) | 2.8 (3.1) | 3.6 (3.9) | 186.0~186.5 | 0.38 | 83 |

TABLE 1-continued

| Compound No. | Structural formula | Elementary analysis *(%) C | H | N | Melting point (°C.) | Amount obtained (g) | Yield (%) |
|---|---|---|---|---|---|---|---|
| 19 | (4-NHSO₂CF₃, 2-C₂H₅ cis thiochroman-1,1-dioxide) | 40.2 (40.3) | 3.8 (3.9) | 4.2 (3.9) | 121.6~123.0 | 0.43 | 100 |
| 20 | (4-NHSO₂CF₃, 2-C₂H₅ trans thiochroman-1,1-dioxide) | 40.3 (40.3) | 3.9 (3.9) | 4.2 (3.9) | 111.0~112.5 | 0.42 | 98 |
| 21 | (6-F, 4-NHSO₂CF₃ thiochroman-1,1-dioxide) | 34.3 (34.6) | 2.4 (2.6) | 3.9 (4.0) | 126.3~129.1 | 0.37 | 88 |
| 22 | (6-F, 4-NHSO₂CF₃, 2,2-diCH₃ thiochroman-1,1-dioxide) | 38.4 (38.4) | 3.4 (3.5) | 3.5 (3.7) | 157.5~158.0 | 0.41 | 90 |
| 23 | (6-F, 4-NHSO₂CF₃, 2-CH₃ thiochroman-1-oxide) | 38.1 (38.3) | 3.1 (3.2) | 4.1 (4.1) | 156.4~158.0 | 0.80 | 77 |
| 24 | (6-F, 4-NHSO₂CF₃, 2-n-C₃H₇ thiochroman-1-oxide) | 43.9 (43.9) | 4.4 (4.5) | 4.2 (3.9) | 202.0~204.2 | 0.20 | 47 |
| 25 | (4-NHSO₂CF₃, N-CH₃ benzothiazine-1,1-dioxide) | 35.1 (34.9) | 3.1 (3.2) | 8.2 (8.1) | 153.0~154.2 | 8.5 | 73 |
| 26 | (4-NHSO₂CF₃, N-C₂H₅ benzothiazine-1,1-dioxide) | 36.9 (36.9) | 3.4 (3.7) | 7.6 (7.8) | 102.2~105.0 | 7.8 | 64 |

*The value in brackets shows the theoretical value.

TABLE 2

| Compound No. | Infrared spectrum*[1] (cm$^{-1}$) | Proton NMR spectrum*[2] (ppm) |
|---|---|---|
| 1 | 3320(NH)1379,1200(SO$_2$) | 2.22(m,1H) 2.30(m,1H) 4.18(m,1H) 4.30(m,1H)<br>4.80(m,1H) 5.15(d,1H) 6.84(d,1H) 6.96(t,1H) 7.19~7.29(m,2H) |
| 2 | 3340(NH)1374,1192(SO$_2$) | 2.19(m,1H) 2.53(m,1H) 3.02(m,1H) 3.17(m,1H)<br>4.86(m,1H) 5.21(d,1H) 7.07~7.30(m,4H) |
| 3 | 3300(NH)1385,1210(SO$_2$) | 2.15(m,1H) 2.50(m,1H) 2.90~3.20(m,2H) 4.80(m,1H)<br>5.15(s,1H) 7.03~7.28(m,3H) |
| 4 | 3345(NH)1380,1204(SO$_2$) | 1.94(m,1H) 2.40(s,3H) 2.65(m,1H) 2.97(m,1H)<br>3.21(m,1H) 5.07(t,1H) 5.13(d,1H) 6.95~7.25(m,3H) |
| 5 | 3340(NH)1390,1210(SO$_2$) | 1.88(m,1H) 2.73(m,1H) 3.05(m,1H) 3.25(m,1H)<br>5.02(m,1H) 5.37(s,1H) 7.15(d,1H) 7.30(d,1H) |
| 6 | 3280(NH)1380,1202(SO$_2$) | 2.20(m,1H) 2.53(m,1H) 3.05~3.19(m,2H)<br>4.93(m,1H) 5.45(d,1H) 7.25(m,1H) 7.48(d,1H) 7.63(d,1H) |
| 7 | 3300(NH)1372,1185(SO$_2$) | 1.03(d,3H) 2.64(m,1H) 2.75(q,1H) 3.42(q,1H) 4.45(q,1H)<br>5.20(d,1H) 7.07~7.27(m,4H) |
| 8 | 3320(NH)1386,1205(SO$_2$) | 1.24(d,3H) 2.31(m,1H) 2.75(t,1H) 3.06(q,1H) 4.64(q,1H)<br>5.34(d,1H) 7.08~7.28(m,4H) |
| 9 | 3340(NH)1380,1215(SO$_2$) | 1.42(d,3H) 1.83(m,1H) 2.45(m,1H) 3.43(m,1H)<br>5.48(d,1H) 5.82(m,1H) 6.90~7.10(m,3H) |
| 10 | 3300(NH)1388,1212(SO$_2$) | 1.38(d,3H) 1.94(q,1H) 2.58(m,1H) 3.50(m,1H)<br>4.81(m,1H) 5.34(d,1H) 6.88~7.18(m,3H) |
| 11 | 3350(NH)1390,1215(SO$_2$) | 1.00(d,3H) 2.60(m,1H) 2.85(q,1H) 3.42(q,1H)<br>4.48(s,1H) 5.40(s,1H) 7.04~7.35(m,3H) |
| 12 | 3320(NH)1375,1210(SO$_2$) | 1.40(d,3H) 1.98(m,1H) 2.28~2.50(m,1H) 3.58(m,1H)<br>4.55~4.77(m,1H) 7.20(s,1H) 7.45(s,1H) 9.60(d,1H) |
| 13 | 3300(NH)1385,1200(SO$_2$) | 0.97(t,3H) 1.50(m,2H) 1.65(m,2H) 1.97(q,1H) 2.56(m,1H)<br>3.42(m,1H) 4.83(m,1H) 5.22(d,1H) 7.10~7.41(m,4H) |
| 14 | 3340(NH)1386,1182(SO$_2$) | 0.97(t,3H) 1.51(m,2H) 1.67(m,2H) 1.88(m,1H) 2.50(m,1H)<br>3.40(m,1H) 4.86(m,1H) 5.25(d,1H) 7.06~7.29(m,4H) |
| 15 | 3325(NH)1375,1182(SO$_2$) | 1.06(t,3H) 1.71(m,2H) 1.97(q,1H) 2.58(m,1H) 3.35(m,1H)<br>4.84(m,1H) 5.20(d,1H) 7.10~7.20(m,3H) 7.40(d,1H) |
| 16 | 3280(NH)1380,1188(SO$_2$) | 1.07(t,3H) 1.75(m,2H) 1.87(m,1H) 2.52(m,1H) 3.33(m,1H)<br>4.88(m,1H) 5.23(d,1H) 7.07~7.28(m,4H) |
| 17 | 3320(NH)1400,1305,1165(SO$_2$) | 1.38(d,3H) 2.43~2.63(m,2H) 3.50(m,1H)<br>4.85(m,1H) 6.82(d,1H) 7.15~7.28(m,2H) 7.75~7.85(m,1H) |
| 18 | 3220(NH)1400,1244,1160(SO$_2$) | 1.52(d,3H) 2.47(m,1H) 2.64(q,1H) 3.50(m,1H)<br>4.85(m,1H) 7.20~7.37(m,2H) 7.93~8.03(m,1H) 9.78(s,1H) |
| 19 | 3220(NH)1398,1244,1160(SO$_2$) | 1.13(t,3H) 1.58(m,1H) 2.20(m,2H) 2.58(m,1H) 3.12(m,1H)<br>4.87(m,1H) 6.37(d,1H) 7.51~7.57(m,2H) 7.63(t,1H) 7.90(d,1H) |
| 20 | 3250(NH)1398,1302,1160(SO$_2$) | 1.10(t,3H) 1.59(m,1H) 2.14(m,1H) 2.48~2.66(m,2H) 3.30(m,1H)<br>4.94(s,1H) 6.36(s,1H) 7.50(d,1H) 7.56(t,1H) 7.63(t,1H) 7.87(d,1H) |
| 21 | 3300(NH)1395,1300,1200,1160(SO$_2$) | 2.77(m,2H) 3.57(m,2H) 4.53(s,1H)<br>4.93(m,1H) 7.32(m,2H) 7.95(m,1H) |
| 22 | 3280(NH)1400,1300,1160(SO$_2$) | 1.45(s,3H) 1.49(s,3H) 2.34(q,1H) 2.82(t,1H)<br>4.80(q,1H) 7.31(m,2H) 7.98(m,1H) 10.0(d,1H) |
| 23 | 3470(NH)1385,1200(SO$_2$)1010(SO) | 1.20(d,3H) 2.01(m,1H) 2.52(m,1H) 3.25(m,1H) 4.65(m,1H)<br>7.11~7.22(m,2H) 7.65(m,1H) 9.02(d,1H) |
| 24 | 3470(NH)1382,1188(SO$_2$)1010(SO) | 0.95(t,3H) 1.54(m,4H) 1.73(m,1H) 1.93(m,1H),3.25(m,1H)<br>4.90(m,1H) 7.45~7.82(m,4H) 10.26(s,1H)*[3] |
| 25 | 3200(NH)1380,1335,1200,1175(SO$_2$) | 2.87(s,3H) 3.74(m,2H) 4.87(m,1H)<br>6.42(d,1H) 7.50~7.75(m,4H) |
| 26 | 3220(NH)1392,1320,1210,1182(SO$_2$) | 1.23(t,3H) 3.12(m,1H) 3.44(m,1H)<br>3.77(m,2H) 4.84(m,1H) 6.45(d,1H) 7.50~7.75(m,4H) |

*[1]KBr tablet method
*[2]Solvent: chloroform-D, Internal standard: tetramethyl silane (TMS)
*[3]Solvent: dimethyl sulfoxide-D$_6$, Internal standard: tetramethyl silane (TMS)

EXAMPLES 1 TO 26 AND COMPARATIVE EXAMPLE 1

(1) Preparation of herbicides

A carrier for wettable powder was prepared by uniformly pulverizing and mixing 97 parts by weight of talc (trade name Zieklite) as a carrier, 1.5 parts by weight of alkyl aryl sulfonate (trade name Neopelex, manufactured by Kao Atlas Co.) as a surface active agent and 1.5 parts by weight of a nonionic and anionic surface active agent (trade name Solpol 800A, manufactured by Toho Kagaku Kogyo Co.).

Herbicides were obtained each by uniformly pulverizing and mixing 90 parts by weight of this carrier for wettable powder and 10 parts by weight of one of the trifluoromethanesulfonamide derivatives obtained in the above described Preparation Examples (or 10 parts by weight of N-benzyltrifluoromethanesulfonamide in Comparative Example 1).

(2) Bioassay (folian treatment)

Seeds of weeds including Digitaria sanguinalis, Echinochloa crus-galli and Ipomoea purpurea and seeds of Gossypium spp were sowed on in upland field soil filled in 1/5000 are Wagner pots and, after covering up with soil, were grown in a greenhouse and an aqueous suspension of the herbicide obtained in (1) described above in a predetermined amount was uniformly sprayed over the foliage in a liquid volume corresponding to 200 liters per 10 ares when these plants were in their single-leaf or double-leaf stage. Thereafter, the test plants were grown in a green-house for 20 days and the herbicidal activity was evaluated. The results are shown in Table 3.

Incidentally, the herbicidal activity and the phytotoxicity to the crops by the chemicals are expressed according to the following criteria.

| Herbicidal activity | Treated/untreated weight ratio of residual weeds, % |
|---|---|
| 0 | 100 |
| 1 | 61–80 |
| 2 | 41–60 |
| 3 | 21–40 |
| 4 | 6–20 |
| 4.5 | 1–5 |
| 5 | 0 |
| Phytotoxicity to crops by chemicals | |
| − | 100 |
| ± | 95–99 |
| + | 90–94 |
| ++ | 80–89 |
| +++ | 0–79 |

EXAMPLES 27 TO 34 AND COMPARATIVE EXAMPLE 2

Soil treatment

Seeds of weeds including Digitaria sanguinalis, Setaria viridis and Cynodon doctylon and seeds of Zea maize, Glycine max and Gossypium spp were sowed in an upland field soil filled with in 1/5000 are Wagner pots and, after covering up with soil, an aqueous suspension of one of the herbicides obtained in the same manner as in the above described Examples 1 to 26 and the herbicide obtained in Comparative Example 1 each in a predetermined amount was uniformly sprayed onto the surface of the soil. Thereafter, the test plants were grown in a greenhouse for 20 days and the herbicidal activity and the phytotoxicity to the crops were evaluated. The results are shown in Table 4.

TABLE 3

| No. | Compound used | Dosage*¹ (g.a.i/are) | Herbicidal activity | | | | Phytotoxicity to Gossypium spp |
|---|---|---|---|---|---|---|---|
| | | | Digitaria sanguinalis | Echinochloa crus-galli | Ipomoea purpurea | Abutilon theophrasti | |
| Example 1 | 1 | 10 | 1 | 1 | 5 | 5 | — |
| Example 2 | 2 | 10 | 3 | 4 | 5 | 5 | — |
| Example 3 | 3 | 10 | 3 | 5 | 5 | 5 | — |
| Example 4 | 4 | 10 | 5 | 5 | 5 | 5 | — |
| Example 5 | 5 | 10 | 1 | 3 | 5 | 5 | — |
| Example 6 | 6 | 10 | 3 | 3 | 5 | 5 | — |
| Example 7 | 7 | 10 | 5 | 5 | 5 | 4 | — |
| Example 8 | 8 | 10 | 5 | 5 | 5 | 4 | — |
| Example 9 | 9 | 10 | 4 | 5 | 5 | 5 | — |
| Example 10 | 10 | 10 | 5 | 5 | 5 | 5 | — |
| Example 11 | 11 | 10 | 1 | 5 | 5 | 5 | — |
| Example 12 | 12 | 10 | 1 | 1 | 4 | 5 | — |
| Example 13 | 13 | 10 | 1 | 1 | 3 | 4 | — |
| Example 14 | 14 | 10 | 1 | 1 | 3 | 4 | — |
| Example 15 | 15 | 10 | 5 | 5 | 5 | 3 | — |
| Example 16 | 16 | 10 | 2 | 4 | 5 | 3 | — |
| Example 17 | 17 | 10 | 5 | 5 | 5 | 5 | — |
| Example 18 | 18 | 10 | 5 | 5 | 5 | 5 | — |
| Example 19 | 19 | 10 | 5 | 5 | 5 | 5 | — |
| Example 20 | 20 | 10 | 1 | 3 | 5 | 5 | — |
| Example 21 | 21 | 10 | 3 | 3 | 5 | 5 | — |
| Example 22 | 22 | 10 | 4 | 5 | 5 | 5 | — |
| Example 23 | 23 | 10 | 5 | 5 | 5 | 5 | — |
| Example 24 | 24 | 10 | 2 | 3 | 5 | 3 | — |
| Example 25 | 25 | 10 | 5 | 5 | 5 | 5 | — |
| Example 26 | 26 | 10 | 5 | 5 | 5 | 5 | — |
| Comparative Example 1 | Formula [A]*² | 100 | 1 | 1 | 1 | 1 | — |
| | | 10 | 0 | 0 | 0 | 0 | — |

*¹gram active ingredient
*²N-benzyltrifuoromethanesulfonamide (the specification of U.S. Pat. No. 3,629,332) represented by the formula

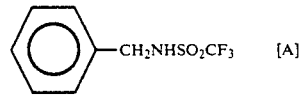   [A]

TABLE 4

| | Compound used | Dosage* (g.a.i/are) | Herbicidal activity | | | Phytotoxicity | | |
|---|---|---|---|---|---|---|---|---|
| | | | Digitaria sanguinalis | Setaria viridis | Cynodon doctylon | Glycine max | Gossypium spp | Zea maize |
| Example 27 | 6 | 5 | 5 | 4 | 4 | — | — | — |
| Example 28 | 7 | 5 | 5 | 4 | 4 | — | — | — |
| Example 29 | 9 | 5 | 5 | 5 | 5 | — | — | — |
| Example 30 | 10 | 5 | 5 | 5 | 5 | — | — | — |
| Example 31 | 17 | 5 | 4.5 | 4 | 5 | — | — | — |
| Example 32 | 18 | 5 | 4.5 | 5 | 4 | — | — | — |
| Example 33 | 21 | 5 | 5 | 5 | 5 | — | — | — |
| Example 34 | 23 | 5 | 5 | 5 | 5 | — | — | — |
| Comparative Example 2 | Formula [A] | 50 | 2 | 2 | 2 | — | — | — |
| | | 5 | 0 | 0 | 0 | — | — | — |

*the same meaning as in Table 3 for g.a.i.

EXAMPLE 35 AND COMPARATIVE EXAMPLES 3 AND 4

Cypeurs rotundus in their six- to seven-leaf stage as grown in 1/5000-are Wagner pots filled with an upland field soil were treated by uniformly spraying an aqueous suspension of a predetermined amount of the herbicide obtained in Example 25 or a predetermined amount of a herbicide obtained by the same procedure as in Comparative Example 1 except Perfluidone or the compound described in the official publication of Japanese Patent Kokai No. 61-221170 were used in place of N-benzyltrifluoromethanesulfonamide used in Comparative Example 1 over the foliage in a liquid volume corresponding to 200 liters per 10 ares. Thereafter, the test plants were grown in a greenhouse for one month and the herbicidal activity was evaluated. The results are shown in Table 5.

TABLE 5

| No. | Compound used | Dosage*[1] (g.a.i/are) | Herbicidal activity |
|---|---|---|---|
| Example 35 | Compound 25 | 5 | 5 |
| Comparative Example 3 | Perfluidone*[2] | 5 | 0 |
| Comparative Example 4 | Compound described in Japanese Patent Kokai No. 61-221170*[3] | 5 | 1 |

*[1] the same meaning as in Table 3 for g.a.i

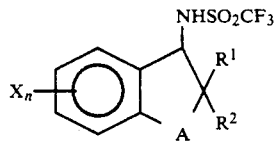

POSSIBILITY OF INDUSTRIAL UTILIZATION

The novel trifluoromethanesulfonamide derivatives of the present invention can be prepared efficiently by the disclosed method and these trifluoromethanesulonamide derivatives are useful as a herbicide for use in an upland field by virtue of the excellent herbicidal activity against weeds including hardly controllable weeds and absence of phytotoxicity against crops in an upland field. Further, they can be utilized as a herbicide in a non-plowed field and a plant growth regulator.

We claim:

1. A trifluoromethanesulfonamide compound represented by the formula

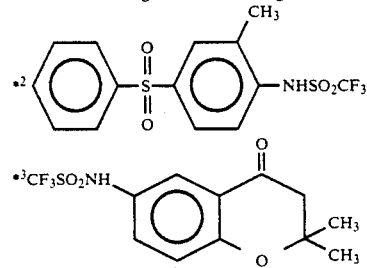

wherein X is a hydrogen atom, a halogen atom, an alkyl group having 1 to 4 carbon atoms or a haloalkyl group having 1 to 4 carbon atoms, n is 1, 2 or 3 and A is $-O-CR^3R^4-$, $-S-CR^3R^4-$, $-SO-CR^3R^4-$ or $-SO_2-CR^3R^4-$ and $R^1$, $R^2$, $R^3$ and $R^4$ are each a hydrogen atom or an alkyl group having 1 to 4 carbon atoms.

2. A herbicide comprising a carrier and a trifluoromethanesulfonamide compound represented by the formula

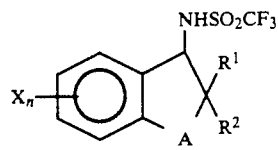

wherein X is a hydrogen atom, a halogen atom, an alkyl group having 1 to 4 carbon atoms or a haloalkyl group having 1 to 4 carbon atoms, n is 1, 2, or 3 and A is $-O-CR^3R^4-$, $-S-CR^3R^4-$, $-SO-CR^3R^4-$ or $-SO_2-CR^3R^4-$ and $R^1$, $R^2$, $R^3$ and $R^4$ are each a hydrogen atom or an alkyl group having 1 to 4 carbon atoms.

3. The trifluoromethanesulfonamide compound of claim 1 selected from the group consisting of

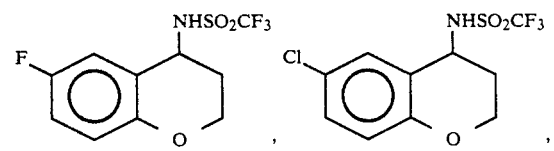
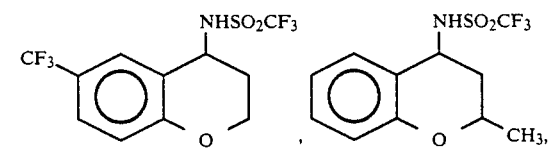
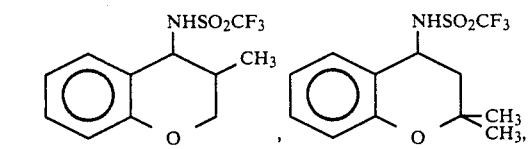
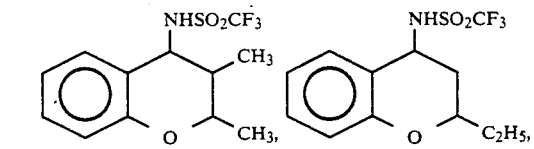
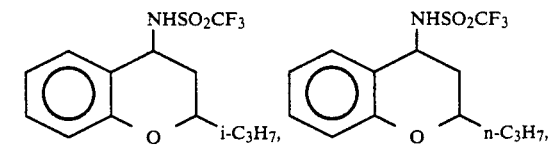
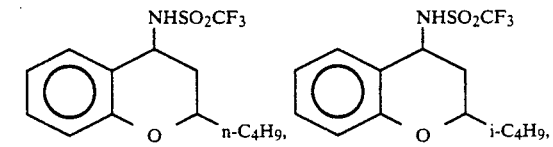
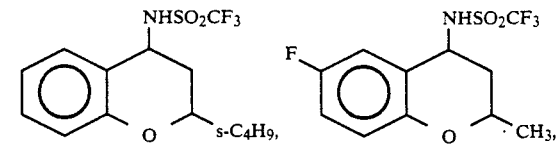

-continued

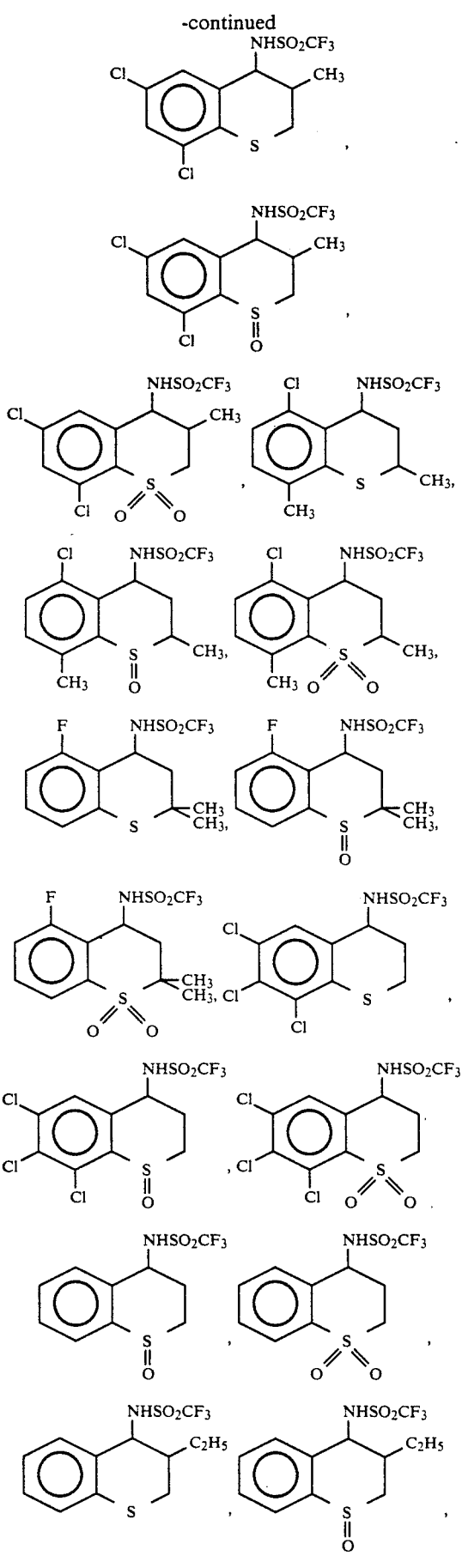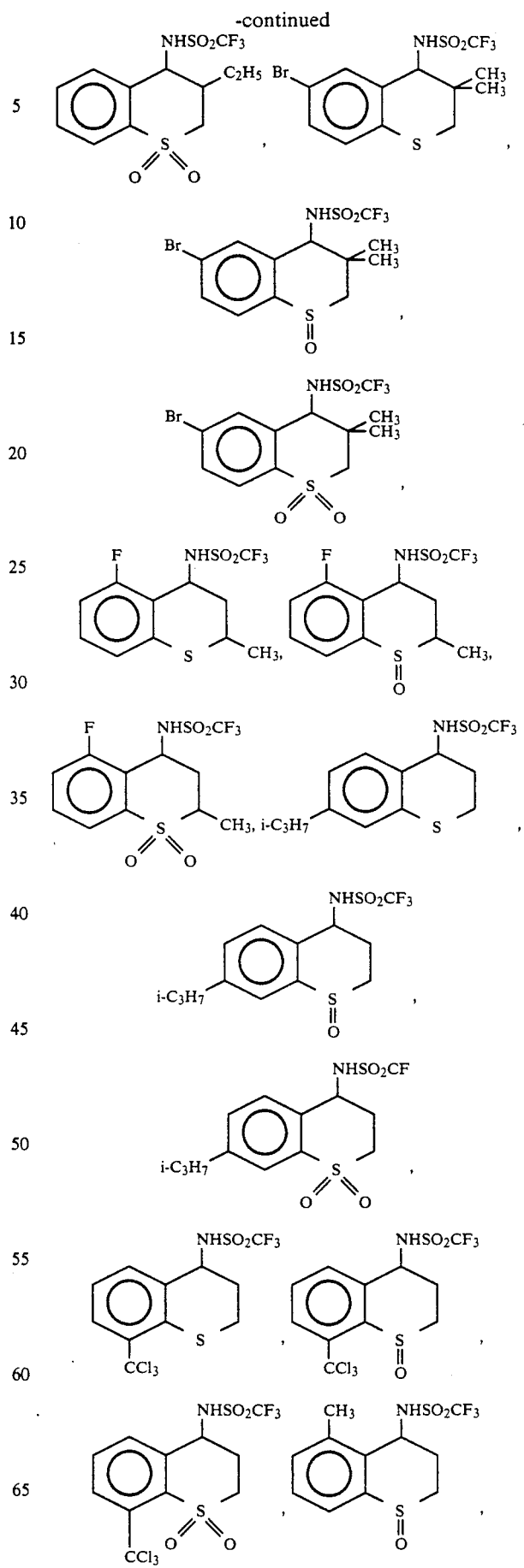

-continued

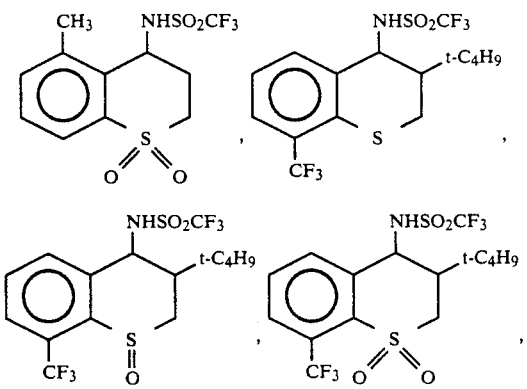

4. The trifluoromethanesulfonamide compound of claim 1 of the formula

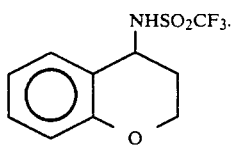

5. The trifluoromethanesulfonamide compound of claim 1 of the formula

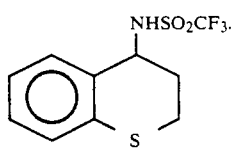

6. The trifluoromethanesulfonamide compound of claim 1 of the formula

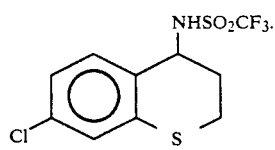

7. The trifluoromethanesulfonamide compound of claim 1 of the formula

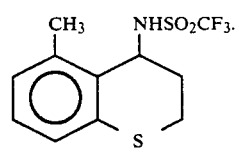

8. The trifluoromethanesulfonamide compound of claim 1 of the formula

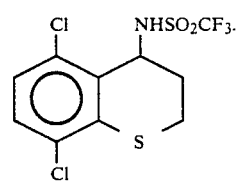

9. The trifluoromethanesulfonamide compound of claim 1 of the formula

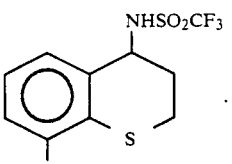

10. The trifluoromethanesulfonamide compound of claim 1 of the formula

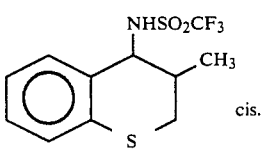

11. The trifluoromethanesulfonamide compound of claim 1 of the formula

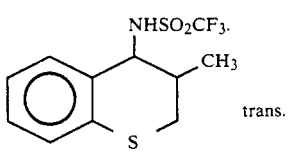

12. The trifluoromethanesulfonamide compound of claim 1 of the formula

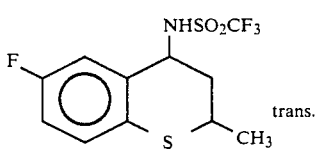

13. The trifluoromethanesulfonamide compound of claim 1 of the formula

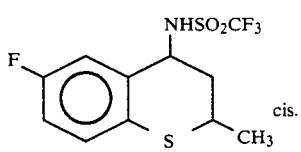

14. The trifluoromethanesulfonamide compound of claim 1 of the formula

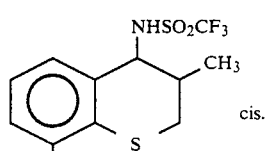

15. The trifluoromethanesulfonamide compound of claim 1 of the formula

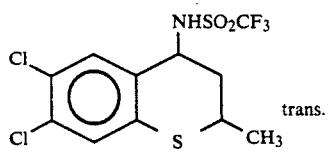
trans.

16. The trifluoromethanesulfonamide compound of claim 1 of the formula

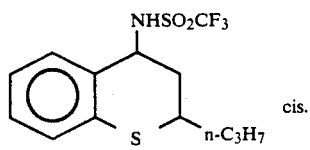
cis.

17. The trifluoromethanesulfonamide compound of claim 1 of the formula

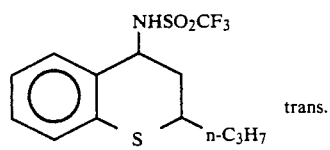
trans.

18. The trifluoromethanesulfonamide compound of claim 1 of the formula

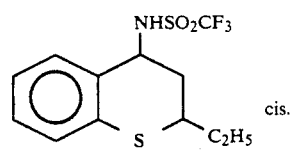
cis.

19. The trifluoromethanesulfonamide compound of claim 1 of the formula

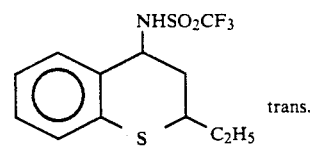
trans.

20. The trifluoromethanesulfonamide compound of claim 1 of the formula

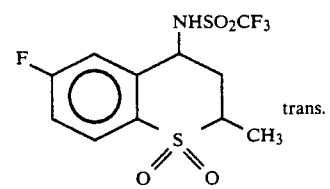
trans.

21. The trifluoromethanesulfonamide compound of claim 1 of the formula

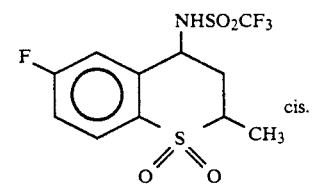
cis.

22. The trifluoromethanesulfonamide compound of claim 1 of the formula

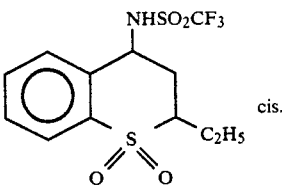
cis.

23. The trifluoromethanesulfonamide compound of claim 1 of the formula

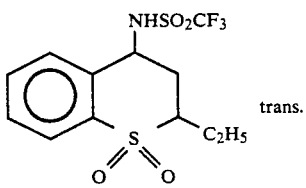
trans.

24. The trifluoromethanesulfonamide compound of claim 1 of the formula

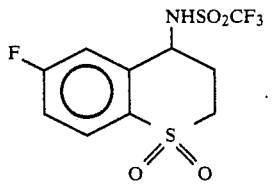

25. The trifluoromethanesulfonamide compound of claim 1 of the formula

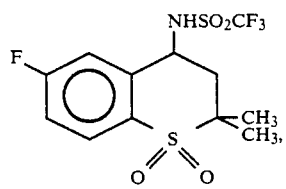

26. The trifluoromethanesulfonamide compound of claim 1 of the formula

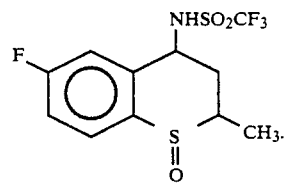

27. The trifluoromethanesulfonamide compound of claim 1 of the formula

28. A method for protecting crops from weeds comprising applying to a site in which the crops are grown a herbicidally effective amount of a trifluoromethanesulfonamide compound of claim 1.

29. A method for protecting crops from weeds comprising applying to a site in which the crops are grown a herbicidally effective amount of a trifluoromethanesulfonamide compound of claim 3.

30. A herbicide comprising a carrier and an effective herbicidal amount of a trifluoromethanesulfonamide compound according to claim 3.

* * * * *

UNITED STATES PATENT AND TRADEMARK OFFICE
CERTIFICATE OF CORRECTION

PATENT NO. : 5,035,739
DATED : July 30, 1991
INVENTOR(S) : SHIBATA et al

It is certified that error appears in the above-identified patent and that said Letters Patent is hereby corrected as shown below:

Title page, item [62] Related U.S. Application Data should read as follows: —[62] Division of Ser. No. 254,935, filed as PCT/JP88/00104, on Feb. 4, 1988, Pat. No. 4,919,705—

Signed and Sealed this

Thirty-first Day of January, 1995

Attest:

BRUCE LEHMAN

Attesting Officer

Commissioner of Patents and Trademarks